United States Patent
Harvill et al.

(10) Patent No.: US 12,299,722 B2
(45) Date of Patent: May 13, 2025

(54) SYSTEM AND METHOD FOR ADJUSTING CUSTOM TOPICAL AGENTS

(71) Applicant: Shiseido Company, Limited, Tokyo (JP)

(72) Inventors: Leslie Y. Harvill, Half Moon Bay, CA (US); Kaialia Morrow, Calabasas, CA (US); Mandy Peiyin Lin, Portola Valley, CA (US); Amy Jo Kim, Burlingame, CA (US)

(73) Assignee: Shiseido Company, Limited, Tokyo (JP)

( * ) Notice: Subject to any disclaimer, the term of this patent is extended or adjusted under 35 U.S.C. 154(b) by 363 days.

(21) Appl. No.: 15/915,009

(22) Filed: Mar. 7, 2018

(65) Prior Publication Data
US 2018/0260871 A1    Sep. 13, 2018

Related U.S. Application Data

(60) Provisional application No. 62/468,345, filed on Mar. 7, 2017.

(51) Int. Cl.
  *G06Q 30/00* (2023.01)
  *A61K 8/18* (2006.01)
  (Continued)

(52) U.S. Cl.
  CPC .......... *G06Q 30/0621* (2013.01); *A61K 8/18* (2013.01); *G06F 3/04817* (2013.01);
  (Continued)

(58) Field of Classification Search
  CPC . G06Q 30/0601–0645; G06Q 30/0621; A61Q 17/04
  (Continued)

(56) References Cited

U.S. PATENT DOCUMENTS

| 5,249,263 A | 9/1993 | Yanker |
| 5,315,508 A * | 5/1994 | Bain ............ G06K 17/00 705/28 |

(Continued)

FOREIGN PATENT DOCUMENTS

| CN | 1443333 A | 7/2001 |
| CN | 1572250 A | 2/2005 |

(Continued)

OTHER PUBLICATIONS

Jang, In-Su, Makeup color reproduction based on spectrum data, Jan. 1, 2013, The 19th Korea-Japan Joint Workshop on Frontiers of Computer Vision, pp. 233-236 (Year: 2013).*

(Continued)

*Primary Examiner* — William J Allen
*Assistant Examiner* — Timothy J Kang
(74) *Attorney, Agent, or Firm* — Calderone McKay LLC

(57) ABSTRACT

Systems and methods herein are developed which enable modification of an initial customized cosmetic product, wherein the initial customized cosmetic product is created based on an initial customized cosmetic product specification or an existing specification of a non-custom product. One such system for making a custom cosmetic product from an existing non-custom cosmetic product is configured to be capable of: characterizing a non-custom product with a known key comprised of at least one search component; providing user interaction to modify at least one of the at least one search components in this key to create a modified key; and using the modified key to produce custom product by evaluating a neighborhood of closest keys to determine manufacturing instructions. Further, a system to modify a custom product is configured to be capable of: specifying a custom cosmetic product by a known key comprised of at least one search component; providing user interaction to (Continued)

modify at least one search component in this key to create a modified key; and using the modified key to produce custom product by evaluating a neighborhood of closest keys to determine manufacturing instruction.

26 Claims, 14 Drawing Sheets

(51) Int. Cl.
*G06F 3/04817* (2022.01)
*G06F 3/04847* (2022.01)
*G06F 16/9032* (2019.01)
*G06Q 30/0601* (2023.01)
*A61Q 1/02* (2006.01)
*A61Q 17/04* (2006.01)
*G06F 16/9038* (2019.01)

(52) U.S. Cl.
CPC ...... *G06F 3/04847* (2013.01); *G06F 16/9032* (2019.01); *A61Q 1/02* (2013.01); *A61Q 17/04* (2013.01)

(58) Field of Classification Search
USPC ............................................. 705/26.1–27.2
See application file for complete search history.

(56) References Cited

U.S. PATENT DOCUMENTS

| | | | |
|---|---|---|---|
| 5,622,692 A | 4/1997 | Rigg et al. | |
| 5,658,915 A | 7/1997 | McKinney et al. | |
| 5,903,465 A | 5/1999 | Brown | |
| 6,177,093 B1 | 1/2001 | Lombardi et al. | |
| 6,510,366 B1 | 1/2003 | Murray et al. | |
| 6,666,216 B2 | 12/2003 | Bourjal | |
| 6,761,697 B2 | 7/2004 | Rubinstenn et al. | |
| 6,856,861 B2 | 2/2005 | Dirksing et al. | |
| 6,985,230 B2 | 1/2006 | De Rigal et al. | |
| 7,061,617 B2 | 6/2006 | Querleux et al. | |
| 7,324,668 B2 | 1/2008 | Rubinstenn et al. | |
| 7,337,127 B1 | 2/2008 | Smith et al. | |
| 7,394,538 B2 | 7/2008 | Bazin | |
| 7,437,344 B2 | 10/2008 | Peyrelevade | |
| 7,634,103 B2 | 12/2009 | Rubinstenn et al. | |
| 8,265,351 B2 | 9/2012 | Aarabi | |
| 8,498,456 B2 | 7/2013 | Legagneur et al. | |
| 8,564,778 B1 | 10/2013 | Igarashi | |
| 8,593,634 B1 | 11/2013 | Igarashi | |
| 8,620,038 B2 | 12/2013 | Aarabi | |
| 8,660,319 B2 | 2/2014 | Aarabi et al. | |
| 8,693,768 B1 | 4/2014 | LaForgia | |
| 8,695,610 B2 | 4/2014 | Samain et al. | |
| 8,725,560 B2 | 5/2014 | Aarabi | |
| 8,830,468 B2 | 9/2014 | Igarashi | |
| 8,856,160 B2 | 10/2014 | Beaver et al. | |
| 8,933,944 B2 | 1/2015 | Aghassian et al. | |
| 9,007,588 B1 | 4/2015 | Igarashi | |
| 9,058,765 B1 | 6/2015 | Mallick et al. | |
| 9,064,279 B1* | 6/2015 | Tuan ........................ G01J 3/50 | |
| 9,064,344 B2 | 6/2015 | Smith | |
| 9,118,876 B2 | 8/2015 | Felt | |
| 9,122,918 B2 | 9/2015 | Howell et al. | |
| 9,122,919 B2 | 9/2015 | Howell et al. | |
| 9,275,400 B2 | 3/2016 | Aarabi | |
| 9,330,298 B2 | 5/2016 | Imai | |
| 9,427,187 B2 | 8/2016 | Gilbert | |
| 9,442,494 B2 | 9/2016 | Igarashi | |
| 9,442,973 B1 | 9/2016 | Tuan et al. | |
| 9,449,412 B1 | 9/2016 | Rogers et al. | |
| 9,460,462 B1 | 10/2016 | Walker et al. | |
| 9,519,927 B1 | 12/2016 | Tuan et al. | |
| 9,639,974 B2 | 5/2017 | Smith et al. | |
| 9,760,935 B2 | 9/2017 | Aarabi | |
| 9,858,473 B2 | 1/2018 | Izumi et al. | |
| 10,083,345 B2 | 9/2018 | Choe et al. | |
| 10,321,748 B2 | 6/2019 | Howell et al. | |
| 10,943,279 B2 | 3/2021 | Stewart et al. | |
| 11,070,793 B2* | 7/2021 | Li ............................ G06T 7/73 | |
| 2002/0049643 A1* | 4/2002 | Church ................ G06Q 10/087 705/37 | |
| 2003/0069667 A1 | 4/2003 | Dirksing et al. | |
| 2003/0149504 A1 | 8/2003 | Iwaki et al. | |
| 2003/0215471 A1 | 11/2003 | Wilmott et al. | |
| 2006/0210154 A1 | 9/2006 | Leveque et al. | |
| 2007/0145126 A1 | 6/2007 | Erlank et al. | |
| 2007/0189627 A1 | 8/2007 | Cohen et al. | |
| 2007/0253987 A1 | 11/2007 | Wozniak et al. | |
| 2008/0199042 A1 | 8/2008 | Smith | |
| 2008/0311061 A1 | 12/2008 | Heuer | |
| 2010/0068247 A1 | 3/2010 | Mou et al. | |
| 2010/0081971 A1 | 4/2010 | Allison | |
| 2010/0123801 A1 | 5/2010 | Son et al. | |
| 2010/0245823 A1 | 9/2010 | Chhibber et al. | |
| 2010/0329995 A1 | 12/2010 | Deeter et al. | |
| 2011/0134275 A1 | 6/2011 | Nguyen | |
| 2011/0211047 A1 | 9/2011 | Chhibber et al. | |
| 2012/0027269 A1 | 2/2012 | Fidaleo et al. | |
| 2012/0188367 A1 | 7/2012 | Marcu | |
| 2012/0216911 A1 | 8/2012 | Bartholomew et al. | |
| 2012/0229828 A1 | 9/2012 | Gill | |
| 2012/0237540 A1 | 9/2012 | Florence et al. | |
| 2012/0251600 A1 | 10/2012 | Yu et al. | |
| 2013/0076932 A1 | 3/2013 | Chhibber et al. | |
| 2013/0148902 A1 | 6/2013 | Hyde et al. | |
| 2014/0081463 A1 | 3/2014 | Igarashi | |
| 2014/0094964 A1 | 4/2014 | Bartholomew et al. | |
| 2014/0267664 A1 | 9/2014 | Gross et al. | |
| 2014/0267665 A1 | 9/2014 | Howell et al. | |
| 2014/0267783 A1 | 9/2014 | Howell et al. | |
| 2014/0288957 A1* | 9/2014 | Grossman .............. G16H 40/67 705/2 |
| 2015/0055086 A1* | 2/2015 | Fonte ..................... B29D 12/02 700/98 |
| 2015/0085279 A1 | 3/2015 | Balooch et al. | |
| 2015/0107678 A1 | 4/2015 | Igarashi | |
| 2015/0339754 A1* | 11/2015 | Bloem ................ G06F 16/9535 705/26.7 |
| 2015/0339757 A1 | 11/2015 | Aarabi | |
| 2015/0346976 A1* | 12/2015 | Karunamuni ....... G06F 3/04817 715/765 |
| 2015/0366328 A1 | 12/2015 | Tamura et al. | |
| 2016/0027087 A1 | 1/2016 | Ahmed | |
| 2016/0107133 A1 | 4/2016 | Sugino et al. | |
| 2016/0125624 A1 | 5/2016 | Liu et al. | |
| 2016/0128450 A1 | 5/2016 | Saito et al. | |
| 2016/0135730 A1 | 5/2016 | Arai et al. | |
| 2016/0174690 A1* | 6/2016 | Howell .................. G06Q 50/22 348/77 |
| 2016/0239187 A1 | 8/2016 | Ben-Bassat | |
| 2016/0316886 A1 | 11/2016 | Samain et al. | |
| 2016/0357196 A1 | 12/2016 | Igarashi | |
| 2017/0011711 A1 | 1/2017 | Campbell et al. | |
| 2017/0020436 A1 | 5/2017 | Flament | |
| 2017/0178220 A1 | 6/2017 | Chong et al. | |
| 2017/0228892 A1 | 8/2017 | Nichol et al. | |
| 2018/0042361 A1* | 2/2018 | Giron .................. B05B 12/1409 |
| 2018/0260871 A1 | 9/2018 | Harvill et al. | |
| 2019/0350345 A1 | 11/2019 | Howell et al. | |
| 2020/0020011 A1 | 1/2020 | Harvill et al. | |
| 2021/0142382 A1 | 5/2021 | Stewart et al. | |
| 2022/0026276 A1 | 1/2022 | Harvill et al. | |

FOREIGN PATENT DOCUMENTS

| | | |
|---|---|---|
| CN | 101112304 A | 1/2008 |
| CN | 101668451 | 5/2012 |
| CN | 105209870 A | 12/2015 |
| EP | 1 196 893 B1 | 9/2003 |
| EP | 1 488 737 B1 | 4/2010 |
| EP | 2 131 697 B1 | 9/2012 |
| JP | 53-009588 A | 1/1978 |

(56) References Cited

FOREIGN PATENT DOCUMENTS

| | | |
|---|---|---|
| JP | 2002-094868 A | 3/2002 |
| JP | 2002-131135 A | 5/2002 |
| JP | 2006106951 A | 4/2006 |
| JP | 2006-254309 A | 9/2006 |
| JP | 2010086036 A | 4/2010 |
| JP | 2012128597 A | 7/2012 |
| JP | 2016-523574 A | 8/2016 |
| WO | 2014/144275 A2 | 9/2014 |

OTHER PUBLICATIONS

Jang, In-Su, Makeup color reproduction based on spectrum data, Jan. 1, 2013, The 19th Korean-Japan Joint Workshop on Frontiers of Computer Vision, pp. 233-236 (Year: 2013).*

International Search Report and Written Opinion from Counterpart International Patent Application No. PCT/2018/021419, dated May 10, 2018, 11 pages.

Extended European Search Report in Counterpart European Application No. 18764135.2, dated Jul. 28, 2020, 8 pages.

Chinese Office Action in counterpart Application 201880023536.1, dated Feb. 8, 2022 with English translation and search report (20 pages).

Chinese Office Action Response in Counterpart Application 201880023536.1, dated Aug. 23, 2022 (15 pages).

Chinese Second Office Action in Counterpart Application 201880023536.1, dated Nov. 2, 2022 and English translation (16 pages).

Chinese Second Office Action Response in Counterpart Application 201880023536.1 dated Aug. 23, 2022.

Chinese Third Office Action in Counterpart Application 201880023536.1 dated Jun. 5, 2023 and English translation (12 pages).

Chinese Third Office Action Response in Counterpart Application 201880023536.1 dated Oct. 20, 2023.

Chinese Notice on Grant in Counterpart Application 201880023536.1 and English language translation dated Dec. 12, 2023 (5 pages).

Response to Expanded European Search Report in counterpart EP18764135.2, dated Feb. 17, 2021 (21 pages).

Japanese Office Action in counterpart Application 2019-548566, dated Apr. 19, 2022 with English translation (9 pages).

Japanese Office Action in Counterpart Application 2019-548566, dated Aug. 4, 2022 (10 pages).

Japanese Final Office Action in Counterpart Application 2019-548566 and English language translation, dated Dec. 6, 2022 (7 pages).

Japanese Notice of Appeal with Amendment and Reasons for Appeal dated Mar. 5, 2023 (17 pages).

Japanese Decision to Grant, dated Jun. 6, 2023 with English Translation (6 pages).

* cited by examiner

SYSTEM AND METHOD FOR ADJUSTING CUSTOM TOPICAL AGENTS

CROSS-REFERENCE TO RELATED APPLICATIONS

This application claims the benefit under 35 U.S.C. § 119(e) to U.S. Provisional Patent Application No. 62/468,345, filed Mar. 7, 2017, the entire disclosure of which is incorporated herein by reference in its entirety.

BACKGROUND OF THE INVENTION

Field of the Invention

The field of the invention relates generally to image analysis and topical agent formulation and, more specifically, to systems and methods for determining a customized cosmetic formulation based on color-calibrated skin images, and further to such systems in which a customer or end user of such formulations can further modify the customized cosmetic formulation using specific user information and feedback from, for example, an interactive user interface.

Description of Related Art

Aesthetic and protective cosmetic topical agents in the form of an applied cream or lotion are widely used to protect against UV radiation, provide a moisture barrier, mask blemishes and skin discoloration, reduce or prevent irritation, and provide other healthful and aesthetic benefits. In the best of all possible worlds, these protective topical agents would be specified by a team of experts for a particular individual with specific needs, and for a specific environment or use. The topical agent would then be formulated in a timely manner and delivered to the individual and the individual could have the possibility to collaborate in the creation of such formulations. Unfortunately, logistics and cost have to date limited the practicality of providing such a specific, optimized product to a given user.

There are several prior art approaches for providing cosmetic topical agents that match a particular need. These agents may be compounded based on a specification from a dermatologist. They may be assembled in a retail store from a set of ingredients by a knowledgeable clerk. Systems or sets of cosmetic creams or lotions with a wide variety of properties may be pre-manufactured and chosen based on a given customer's coloration, skin type, and specific needs.

The main barrier to a general solution for the custom manufacture and distribution of these topical agents is that the number of features in the product are many, and the needs are quite varied. It is also not commercially feasible to manufacture and stock each formulation with the granularity that is optimum for a given need and individual. A need in the art arose for ways to provide useful compounds based on a determination of an individual's specific needs using, for example, advanced image analysis techniques, and formulations that are optimal for that set of needs.

Techniques to capture the reflectance spectra of a surface with moderate specular reflectance and predominately diffuse reflectance can require measuring the reflected color as RGB triplets, or measuring the reflected spectra of the surface using optical methods to integrate the reflectance with a known light source at a known distance with a detector that has been set to a fixed aperture, fixed integration optics, and measured over a fixed period of time. Devices that use these techniques are reflection spectrophotometers and colorimeters.

Some mobile devices have many of the characteristics of the colorimeter. For instance, they have a light source with known characteristics, a CCD detector, a processor, and a lens system that can be used for integration. The primary barriers to using mobile devices as accurate colorimeters are the need to: (1) control ambient light; (2) set the distance to the surface to be sampled; (3) control the aperture used for measurement of the sample; (4) control the detector sensitivity used for measurement of the sample; (5) control the time used for measuring the sample; (6) control the white balance for measuring the sample; and (7) control the focal plane for measuring the sample.

While cameras used in mobile devices have become the most popular handheld cameras presently in use, they generally lack the ability to manually set aperture, and the most popular devices do not allow software to set aperture, sensitivity, or exposure times, although some now allow for the setting of exposure, exposure time and sensitivity. While the hardware and firmware of the mobile device may report what camera settings are used as data embedded in a resulting digital image file, techniques are often used within the firmware to enhance or improve the image, and adjust the white balance. The firmware that controls the camera has been generally optimized to produce quality snapshots, not to make reliable measurement of light and color.

Systems and methods were thus developed to address these issues and allow a user to capture accurate, repeatable color samples using a mobile device. A formulation for an aesthetic and protective topical agent optimized for a specific use was developed by the applicant herein and is disclosed in U.S. Pat. Nos. 8,933,994, 9,122,918 and 9,122,919. The implementation of this and other systems are now being used in industry, and are available in the marketplace. Companies such as MATCHCo. provide a full-stack solution to produce such agents. The system and method disclosed in U.S. Pat. No. 8,933,994 has many benefits, not only in enabling the practical production of these aesthetic agents, but in the ability of such systems and methods to characterize a given user's characteristics and use these characteristics to derive a specific formula. Thus, a new formulation can be particularly formulated based on such systems for an individual user.

While systems such as those described in U.S. Pat. Nos. 8,933,994, 9,122,918 and 9,122,919 may provide an accurate match for a user based on user interaction and scanning previously described, there is further a need in the art to address the issue of how to respond to the user should the user decide he or she wishes to modify the requirements of a specifically matched formulation for aesthetic, environmental, or cultural reasons and also to provide a basis for a user to evaluate their profile and determine if a change should be made after receiving a customized cosmetic. A user may also fall outside of the collected dataset used to construct such a system as described in U.S. Pat. No. 8,933,994. Thus, it would be desirable to develop and provide a method for a user to provide additional input in such a system to adjust an existing agent which may be characterized as described in patent U.S. Pat. No. 8,933,994.

Adaptive systems have been developed that employ a user interaction to iterate toward a user's intent. For instance, there are well-known methods to select color for a specific use. Some are as simple as selecting a colored tile or square, and seeing it applied interactively to an image or product in a computer interface. A useful description of color picking may be found in J. Koenderink et al., "Color Picking: The Initial 20s," ACM Transactions on Applied Perception, Vol. 13, No. 3, Article 13, pp. 13/1-13/25 (2016). Early patents which describe choosing color in an interface, include, for example, U.S. Pat. No. 5,249,263.

As described in Koenderink, supra, such prior art color-picking methods provide an interface for selection of color for display, rather than for manufacturing.

Other methods apply a set of variables to a graphic filter, and present many variations of these variables in an array of rendered choices. On user selection of a set of variable values, a new set of selections may be presented based on a data model, such as described in G. Jalal et al., "Color Portraits: From Color Picking to Interacting with Color," CHI 2015 Proceedings of the 33rd Annual Association of Computing Machiner (ACM) Conference on Human Factors in Computing Systems, pp. 4207-4216, Seoul, Republic of Korea (Apr. 18-23, 2015).

Other techniques use genetic algorithms to learn how a user interacts and to provide interactions that are more intuitive. See, S. Matsui et al., "Genetic Algorithm Can Optimize Hierarchical Menus, CHI 2008 Proceedings of the SIGCHI Conference on Human Factors in Computing Systems, pp. 1385-1388, Florence, Italy (Apr. 5-10, 2008).

U.S. Pat. No. 8,856,160 describes a method to associate user choice of a key-value attribute for a customizable product, matching the key-value to at least one other key-value and selecting a filter, filtering that key-value selection, and applying it to the product.

U.S. Patent Application Publication No. 2008/0311061 A1 describes an apparatus for gathering color data from a user, comparing that color information to set of stored color data, and mixing pigments for a custom product based on the comparison of the user data and the stored data.

Despite such prior art systems, none address a need in the art for a method and system that allows a user to modify an existing customized cosmetic formulation through an interactive user interface so as to automatically create a new and/or modified customized cosmetic formulation.

BRIEF SUMMARY OF THE INVENTION

To modify or adjust a custom cosmetic at a specific time or place, or to produce an adjusted product from an existing non-custom product, there is a need to employ a specific set of the embodiments described in U.S. Pat. Nos. 8,933,994, 9,122,918 and 9,122,919, each of which is incorporated herein by reference in relevant part. This same mechanism may be used and modified to adjust an aesthetic agent to a user's specification, and to map the user's characteristics and specifications to additional products.

In particular, the same mechanism is useful for describing a scanning operation for collecting a specific user's characteristics to be performed on a separate device from the manufacturing device or system, and for that device to communicate the scan information to a server, and for that information be associated with that user on a data store on that server. In this way, scanning data may be used for editing later.

That mechanism is further useful for the server to transform the user scanning data into a form that may be used to find or calculate instructions for manufacture for a variety of cosmetic products. This data form will be called the "key" and is as described in U.S. Pat. No. 8,933,994.

Since there may be many different forms of cosmetic products, and many different manufacturers, it is useful to have a separate action performed on a server that will use a specific user's key to find or calculate instructions for manufacturing a specific cosmetic product.

It is also preferred and further useful for the manufacturing apparatus or system to be separate from the device that generates instructions for manufacturing, since these may be in different locations, manufacture different products, or use different manufacturing processes.

While there are prior known techniques to provide interaction for a user to choose a variation in color, increase or decrease a specific setting as described above, or to choose a different setting to affect a modification, each of these prior techniques is specific to the data model being modified. The data model in the present invention is the user characteristics encoded in the scan data, and that is transformed into a "search key". Its application is in deriving a specific customized cosmetic formula (associated with an OAPTA specification as described herein) using the methods described in U.S. Pat. No. 8,933,994 and herein. Since that data model and system of application are unique, the interaction choices presented to the user will be unique as determined by that data model.

The system disclosed herein differs from prior systems in that the user employing the present invention will already be associated with a search key as that term is defined in U.S. Pat. No. 8,933,994 and herein. The search key is also not in key-value form. More particularly, the search key itself is modified directly, without filtering. The interactive choices presented to the user herein to modify the search key are based on data found within a "ground truth dataset." The system described herein is further unique in comparison with the prior art discussed above in that it collects user data on a separate apparatus, and in a separate process transforms the user scan data into a search key. It then provides another process or interaction to modify the search key and/or to add an additional search key for the same user, preferably, the search key is modified to include different or additional data. The search key as before modification, after modification may then be used to produce a multiplicity of products with different formulas.

The invention herein includes a system to make modified customized cosmetic product from an existing customized cosmetic product or a non-custom cosmetic product by: characterizing the existing non-custom product or customized cosmetic product with a known search key comprised of at least one search component; providing user interaction to modify at least one search component in the known search key to create a modified search key; using the modified search key to produce a modified custom cosmetic product by evaluating a neighborhood of closest keys to determine manufacturing instructions for the modified custom cosmetic product. The complete search key components may include one or more individual search key component(s).

In one embodiment, the at least one search component preferably includes a color component.

In a further embodiment, the at least one search components may comprise a coverage component. Further, the at least one search component may comprise a dryness component.

Each user interaction is preferably based on the selection of a search component to modify in the search key. The user interaction direction is preferably also based on past likelihood of the edit direction.

The user interaction amount may be based on the change of a key component within the neighborhood of the closest keys.

The manufacturing instructions may comprise an amount of each cosmetic primary component, wherein each cosmetic primary component is a valid cosmetic product that meets certain regulatory requirements. In such an embodiment, two measurements are preferably made and recorded to verify the proportions of the primary components. In one embodiment, one of the search components may be a SPF value. The customer contact information may also be associated with the record.

In the system, the known search key is preferably associated with a user and the user interaction may further include using a device having an optical sensor to submit updated user image data to the system for updating data associated with the known search key, and wherein the updated image data is employed in the system to optimize the known search key and the modified search key. The modified search key and known search key are preferably each stored in the system and associated with a user. The user interaction preferably includes interactive selection on an user interface of a slider, button, or image to modify at least one search component.

In a further embodiment herein, the invention includes a method for modifying a customized cosmetic product associated with a user, comprising: a) providing a system configured to be capable of specifying an initial customized cosmetic product of a user by a known search key comprised of at least one search component; b) providing an interactive user interface that allows a user to modify at least one search component in the search key to create a modified search key; and c) using the modified search key to produce modified customized cosmetic product by evaluating a neighborhood of closest keys to determine manufacturing instructions.

In the method the initial customized cosmetic product and known search key are preferably associated with a search key of a non-custom product in the system. The search component may be one or more of a color component, a coverage component and/or a dryness component. Further, in the method, the user interface may include different aspects for the user to interactively modify the search component, including in one embodiment one or more sliders, each associated with a search component and in another embodiment one or more close alternative choice icons displayed adjacent an icon representing one of the search components of the known search key for a user to select for modifying the search component.

In the method, the system preferably collects data associated with the search components of the known search key through a device having an optical sensor and an application that interactively guides a user to scan a calibrated image and transmits data from the scan to the system. The device preferably further comprises a light source.

Also in the method, the scan preferably further provides data associated with the device to the system and the application controls at least one device setting such as aperture, exposure, exposure time, focus, sensitivity, and/or white balance. The system used in the method preferably comprises an order management service including a ground truth database, the application for a user for interacting with the device having an optical sensor, a mixture service, a print service, a dispensing application, a shipping application, and a printing application.

BRIEF DESCRIPTION OF THE SEVERAL VIEWS OF THE DRAWINGS

The foregoing summary, as well as the following detailed description of preferred embodiments of the invention, will be better understood when read in conjunction with the appended drawings. For the purpose of illustrating the invention, there is shown in the drawings embodiments which are presently preferred. It should be understood, however, that the invention is not limited to the precise arrangements and instrumentalities shown. In the drawings, like reference characters generally refer to the same parts throughout the different views. Further, the drawings are not necessarily to scale, with emphasis instead generally being placed upon illustrating the principles of the invention.

In the drawings.

DETAILED DESCRIPTION OF THE INVENTION

Figure 1:
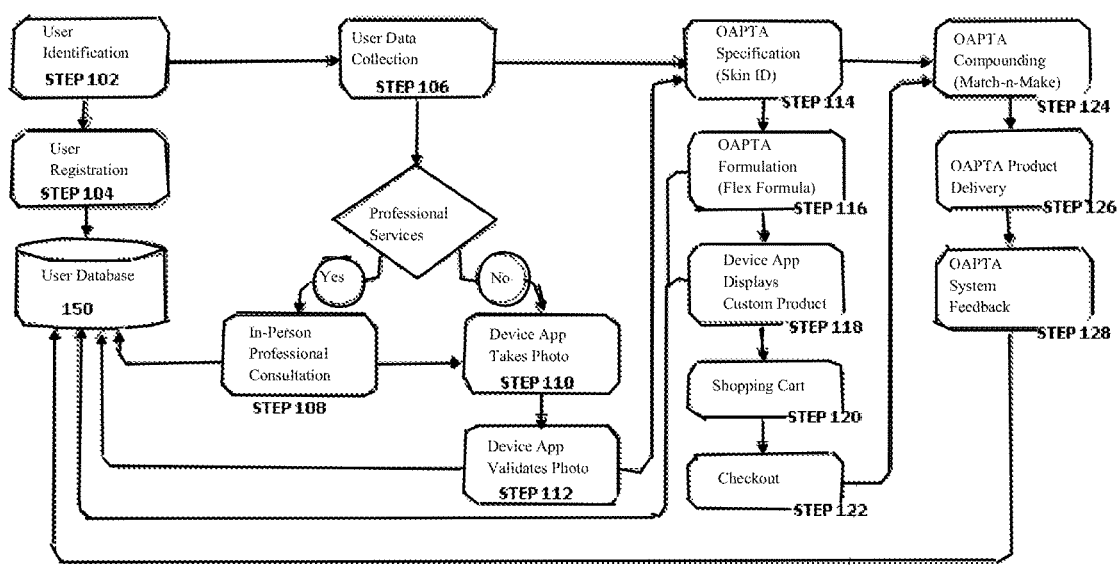
FIG. 1 is a flowchart of an example method for providing an optimized topical agent to a user that may be used by a user to create an initial user profile in the invention.
Figure 2:
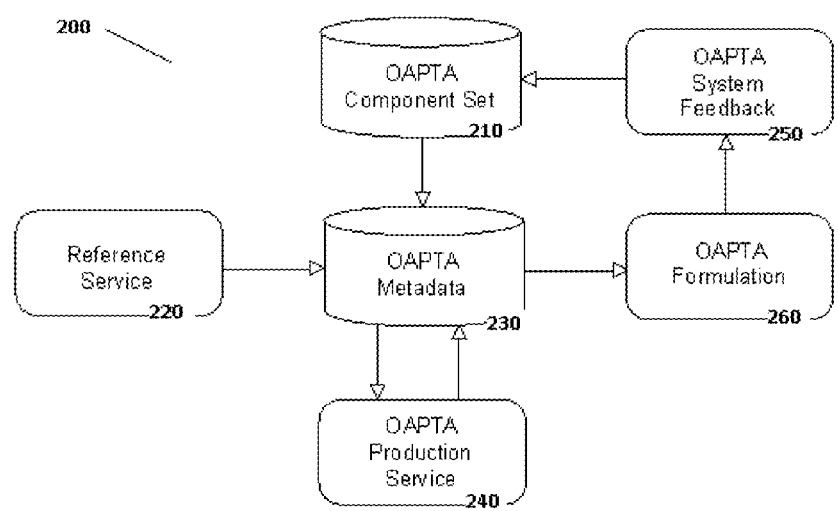
FIG. 2 is a high-level architecture diagram of an example system for providing an optimized topical agent to a user for use in the invention.

The following Description is directed to a new invention and incorporates by reference in relevant part as relates to the underlying systems and methods used for preparing an initial search key as part of a preferred method for creating an initial search key and for calibrating a device as well as other related steps as noted herein each of U.S. Pat. Nos. 8,933,994, 9,122,918 and 9,122,919, each of which is incorporated herein in its entirety to the extent relevant to the disclosure being made herein, and wherein definitions therein from those patents are used in the same manner herein unless otherwise modified herein, and wherein the text is incorporated as applicable to define the prior systems and methods therein which are useful to be employed in the present invention.

In one example of a system that may be used as described above, the customized cosmetic formulation is assembled from some number of primary components. Each of these primary components is a cosmetic that meets applicable regulatory requirements. In this embodiment, the ground truth dataset used for making an initial existing customized cosmetic formulation or that includes an existing non-customized cosmetic formulation is built from scanning and matching a set of reference users, the dataset contains records including the proportions of the primary components used to mix an initial customized cosmetic formulation for the reference user (this will be referred to in some places generally herein as the "mix"), calibrated data generated from the scan (this is called the "key," and further data which may be collected from the user, such as a SPF and/or a "product finish" (i.e., the optical quality of product on the skin). The key includes, at least one search component, which may be, but is not limited to color information, amount of skin dryness, and amount of coverage needed.

In this embodiment, an algorithm is used to search the ground truth dataset and find a mix using a search key. The algorithm is selected to perform at least the following steps: (a) it traverses entries in the ground truth dataset and finds the record whose key is closest to the search key; (b) it finds those records that are nearby, and assembles them into a set called a neighborhood; (c) it solves for the contributions from each entry in the neighborhood that best matches the search key; and (d) it uses the found contributions to calculate the mix formula.

The preferred steps to produce the customized cosmetic formulation for a given search key include: using the algorithm to find the mix formula for the search key; using the mix formula to dispense the primary components into a container; using at least two methods to verify the quantity dispensed, such as a manual operator check, a verification by an automated process using weight, and/or a verification by an automated process using volume; and blending the mixture in the container.

In such an embodiment, at the outset, the user has to create an initial customized cosmetic formulation, which steps may include providing initial feedback to the system by identifying an existing non-custom product being used, various user preferences and other user data as described in detail below. The same steps used for creating the initial customized cosmetic formulation may also be used if the user wants to create a new and separate formulation or wishes to modify the formulation after creating the initial customized cosmetic formulation. As described in the patents noted above that are specifically incorporated herein by reference, the user will initially have to run an interactively guided scan which may be done in several different ways. In one method, a user is preferably guided interactively through a set of steps to produce a customized cosmetic product. For example, the user scans herself or himself using a mobile device and an application acts to interactively guide the user to scan areas of the user's face. In the scan process, a user is guided to capture an image of a skin region with known lighting and color characteristics. That image is processed to provide calibrated skin color information. The system then automatically determines a customized cosmetic formulation for the user based on the calibrated skin color information.

The skin region image is preferably received from a device having an image sensor, and more preferably an image sensor and light source, and the user can be interactively guided through capture of a plurality of skin region images such as facial regions using the device image sensor and/or light source. An "image sensor" may be any image sensor such as a device having a CCD Array to sense light photons and a lens to project an image, software and an image processor, although any suitable image sensor capable of carrying out the functions herein may be used.

Another way of initially carrying out a scan for creating a customized cosmetic formulation, as described in the patents noted above, includes interactively guiding the user through capture of an image of a marker using the device image sensor, and the skin region image is processed based at least in part on the captured marker image. The device used in these scanning and//or image capture steps can be one or more of a mobile phone, a tablet, a digital camera, a webcam, smart glasses, a television, virtual reality goggles, a gaming console, or home assistants (such as Alexa™ or Google® Home™), which preferably have camera and light sensor requirements, and more preferably a light source. The skin region image can include embedded data identifying properties of at least one of the device and the image sensor and the skin region image can be processed based at least in part on the embedded data. The marker used for calibration may be a variety of things, for example, a previously analyzed skin region (or data taken from a variety of samples of skin regions of users), a marker of known size on a white background, or marker that is a white sheet of paper of known size, such as a typical sheet 8.5 inch×11 inch sheet of white paper. The marker should have a known reflectance and color, although the size or standardized reflectance and color could be varied. A sheet of paper having known color, reflectance and size can be used to calibrate the device and its settings, for example to adjust the settings of the camera on a mobile smart phone. Thus, the white sheet of paper acts as a white field and a marker. The user places the paper on a white surface and then proceeds as instructed interactively to calibrate the device.

In calibrating the device or in completing a scan, the user preferably touches the device to a calibration surface, which may be a marker or a skin region (that is, a marker surface is the surface of whatever is used as a basis for calibration). A calibration surface is preferably flat or reasonable flat, but could be any suitable calibration surface. Each touch is considered a "tap." Each movement towards the surface of the marker or skin region to tap and each motion back away from the surface is a single "pass". A complete touch process or "tap" includes two passes and the touch to the surface. The device should be moved so the image sensor's field of view covers at least about 90% of a sheet of a white paper marker. During a tap of about 1 second, about thirty images/second may be recorded and the brightest frame is selected. The data is analyzed by Histogram by brightness and the pixels are analyzed for brightness, shininess and other property differences. Each pass gives a sample of data for analysis.

The user is preferably directed through this process using the application and either video, photos, voice commands or other prompts to performing the tapping. Each scan is evaluated by the application and is composed of at least 5 taps (providing 10 samples during each pass) and sometimes more. After 5 samples are taken, new samples are compared with other samples to perform a running median filter. The filter encourages the collection of samples that fall in the median by discarding those samples that are too light or too dark as compared with the median of the existing samples. Samples that are too distant in color are also discarded. If too many samples are out of calibration range, the application software will ask the user to perform the first step again and begin or continue tapping. The software will continue the scan process until enough valid samples are collected or until the process fails. Users may leave scanning at any time.

Should calibration fail for some reason (such as for poor device performance), the application may instruct the user to continue to tap to try for better data, and will re-set the device to try again, however, if that continues to fail, a customer service contact information option may be provided.

One preferred method of running a scan is described herein. For recording accurate, and reproducible color (that may be repeated), the application software is set to control the exposure of the camera, the amount of light used to measure the surface of the user's skin, and the angle and distance of the camera from the surface of the skin. The software effectively "re-purposes" the device's characteristics for running the scan and further directs user actions.

Each device has an image sensor (camera) and preferably a light source, such as an LED torch. In such a device, the separation of the LED torch and camera, as in a typical mobile smart phone, and its relation to a flat surface to be measured describes a geometry such that there is a single distance from the camera to the target where illumination is brightest. To place the phone at that point, the software will interactively guide the user to make a pass to touch the surface to be measured. As the phone mores towards the surface, the software analyzes each video frame from the camera and finds the time at which the specific region of the image is brightest. This is a known distance from the surface. The surface may be a simple calibration marker as described herein and/or a region of the skin to be measured.

As noted elsewhere herein, a marker may be a piece of white paper with known reflectance and known size (such as white 8.5×11" copy paper of Euro brightness 104) for consistency in size and reflectance as well as widely known use and availability. The use then makes multiple passes ("taps") to measure the surface. Measurements are taken with each pass to and from the surface in the tap. The data is gathered during the tapping and the software may find the specular reflection of the LED torch in the surface of the skin and measure shininess of the surface. It may also be pulled back until the camera focuses on an area of skin and record a micrograph of the skin.

Another way of creating a customized cosmetic formulation can include matching the calibrated skin color information to a reference user, the reference user having a previously determined cosmetic formulation associated therewith.

The automatic determination of the customized cosmetic formulation can be based at least in part also on user input information, for example, on an indication by the user of an allergy to a cosmetic ingredient. A topical agent based on the customized cosmetic formulation can be compounded and delivered to the user. The user can be allowed to purchase a topical agent compounded based on the customized cosmetic formulation.

A user search key as noted herein (which is associated with a user's customized cosmetic formulation) may be associated with an existing non-custom cosmetic product that the system selected as a best match when creating an initial customized cosmetic formulation. The user may thus provide as user initial information (user data collection) to develop the initial customized cosmetic which is associated with the search key. The user may also provide product preferences as feedback to the user's profile for use in modifying the initial customized cosmetic formulation as described herein The user may further perform a transaction to order the product. The data collected from the scan (scan information) is also communicated to a server. The system used in the above-noted methods for creating an initial customized cosmetic formulation includes at least one computer that includes a memory for storing computer-executable instructions and a processing unit for executing the instructions stored in the memory. The execution of the instructions configures the computer to perform operations including guiding a user to capture one or more image(s) of at least one skin region with known lighting and color characteristics. The image is processed to provide calibrated skin color information, and the system automatically determines a customized cosmetic formulation for the user based on the calibrated skin color information. The skin region image(s) can be received from a device having an image sensor, and preferably also a light source, and the operations can further include interactively guiding the user through capture of a plurality of skin region images, such as facial regions using the device image sensor as noted above.

In the MATCHCo. application developed based on the patents incorporated herein by reference, a preferred interactive scanning is carried out using known lighting which is identified by using a device that preferably has a lighting source as well as an image sensor, such as a mobile phone with an LED torch, having known color characteristics. The lighting and color on the skin is further controlled by using the geometry created between the device's position with respect to the surface of the skin and the light source position to determine the distance of the device from the surface of the skin. This is done by interactively guiding the user through a series of actions for each facial region. The user is asked to move the device toward and away from a given facial region, i.e., by making a pass including a "tap," and the distance is detected using the brightest point of illumination of the skin by the light source. For example, the application will run and prompt the user to turn on the device's light source (such as to turn on the LED torch of a mobile smart phone) or use software commands to turn on the light source of the device such as the LED torch automatically, and to move the device towards a particular skin region and away from that region until the brightest point of illumination is recorded through a series of interactive steps. This data is then used to capture calibrated skin color information.

The methods and systems noted above may also have operations that further include interactively guiding the user through capture of an image of a marker using the device image sensor, and the skin region image is processed based at least in part on the captured marker image. The device may be any of those noted above. The skin region image may include embedded data identifying properties of at least one of the device and the image sensor, and the skin region image can be processed based at least in part on the embedded data.

One of the operations carried out in the method and using the system may also include automatically determining the customized cosmetic formulation by matching the calibrated skin color information to a reference user, the reference user having a previously determined cosmetic formulation associated therewith. The customized cosmetic formulation may also be automatically determined based, at least in part, on an indication by the user of an allergy to a cosmetic (or other user preference) so that the operations carried out can further include allowing the user to purchase a customized cosmetic formulation that accommodates those preferences (omitting an ingredient for example).

The user scan may also be carried out in a method for determining a customized cosmetic formulation that includes interactively guiding a user through capture of one or more images using a device having an image sensor and preferably also a light source, wherein each image comprises a skin region of the user, processing the skin region images to provide calibrated skin color information, comparing the calibrated skin color information to a ground truth data set to identify a set of closest known values in the ground truth data set, and automatically determining a customized cosmetic formulation for the user based on the comparison. The customized cosmetic formulation includes at least one of (i) a unique customized cosmetic formulation that is derived based on a relative proximity of the calibrated skin color information to the set of closest known values and (ii) an existing non-customized cosmetic product.

The operations carried out by the systems and methods may include processing the skin region images to include, for at least one of the skin region images: detecting a plurality of facial regions in the at least one skin region image, by various means including by using facial recognition software, segmenting the facial regions based on skin tone, and assigning a color to each facial region segment based on at least one of skin tone, shadow and specular highlight. One such facial recognition software that may be implemented for this purpose is described in U.S. Patent Application Publication No. 2017/0076474A1. Other known facial recognition software may also be employed for this purpose.

In carrying out the various methods and systems herein that involve scanning the user's data, the skin region(s) to be scanned are preferably one or more, or all of, an underside of a wrist, a forehead, a right cheek, a left cheek, a right jaw, a left jaw and/or optionally a full face, although other areas may also be used depending on how the system is designed for optimal use.

The methods and systems may further include allowing the user to purchase an existing cosmetic product based on the initial customized cosmetic product (i.e., one that is based on a unique customized cosmetic formulation or a matched existing non-custom product) or based on any separate, new customized cosmetic product or new a modified customized cosmetic product, each of which is based on an initial customized cosmetic product.

A customized cosmetic formulation may also be determined using a system that includes at least one computer that itself includes a memory for storing computer-executable instructions and a processing unit for executing the instructions stored in the memory. The execution of the instructions configures the computer to perform operations including interactively guiding a user through capture of one or more images using a device having an image sensor, and optionally a light source, wherein each image comprises a skin region of the user; processing the skin region images to provide calibrated skin color information; comparing the calibrated skin color information to a ground truth data set to identify a set of closest known values in the ground truth data set; and automatically determining a customized cosmetic formulation for the user based on the comparison. The customized cosmetic formulation may include at least one of (i) a unique compound of a customized cosmetic formulation that is derived based on a relative proximity of the calibrated skin color information to the set of closest known values and (ii) a match to an existing cosmetic product.

The skin region images used above can be processed so as to include the step of, for at least one of the skin region images: detecting a plurality of facial regions in the at least one skin region image and segmenting the facial regions based on skin tone; and assigning a color to each facial region segment based on at least one of skin tone, shadow, and specular highlight.

Ambient lighting information associated with at least one of the skin region images may also be received, and the at least one skin region image can be processed based at least in part on the ambient lighting information. Such image processing may include use of facial recognition software to process the ambient lighting information to remove ambient lighting to correct the color to one true to the calibrated settings.

The system and methods herein may also further include the steps of interactively guiding the user through capture of an image of a marker using the device image sensor and optionally a light source on the device, and then processing the skin region images based at least in part on the marker image. The current settings of the device image sensor can be stored based on a successful capture of the marker image. The device image sensor settings can include, among other things, aperture, exposure, exposure time, focus, sensitivity, and/or white balance. The skin region images can be processed based on the stored image sensor settings. Processing the skin region images can include compensating for unknown light sources.

The scanning of the user may also be done using a method of capturing accurate color of an object using a device having an image sensor, and optionally a light source, that includes calibrating a plurality of settings of the device using a marker having a known size and/or a known color; measuring a color of each of a plurality of surfaces of the object; determining a surface reflectance of the object based on the measured colors; and determining a surface color variation of the object based on the calibrated settings, the measured surface colors, and the surface reflectance of the object. The plurality of surfaces can include regions of skin, and the device and marker may be as described above.

The device may be calibrated by, for example, directing a user to place the marker on a substantially white field. Calibrating the device can then include setting, based on a captured image of the substantially white field, at least one of aperture, sensitivity (based on ISO unit for measuring sensitivity), exposure time, exposure and/or white balance of the device. Calibrating the device can also include setting a light associated with the device image sensor, such as a mobile phone LED torch, to a known brightness. This allows for control of the white balance and allows for setting of the exposure of the device image sensor, e.g., in the case of a mobile smart phone, the camera's exposure is adjusted. Calibrating the device may also include interactively guiding a user to position the device image sensor at a specific distance from a surface of the marker. Calibrating the device may also further include, upon the positioning of the device image sensor at the specific distance from the surface of the marker, locking at least one of the settings of the device. The settings of the device can be automatic exposure, exposure time, sensitivity, automatic focus, and/or automatic white balance. The locked settings of the device can be applied while measuring the color of each of the surfaces of the object.

In device calibration in one preferred embodiment, using a mobile smart phone camera having an LED torch, each such device is manufactured with a high degree of quality control, and so individual devices of a similar model perform similarly. However, each model has a different set of capabilities and components, such that there are large differences in illumination and exposure characteristics from one model to another. Each model has a particular CCD component. Different CCD components have a different response to light. Each model has a different LED array illuminant component, each LED component produces different light spectra. Further each model may have a specific version of operating system software that acquires the image and adjusts the illumination. For each model of phone and for each major operating system version, it is necessary to have a method of calibrating the response of the camera to the LED illuminant. One embodiment of calibration of the system is that it calibrates the response of the CCD to the light separately from its specific response to skin color. The CCD's response to the LED torch's illumination is performed by using a scanning method as described above (using a calibration surface and tapping) to measure a set of known gray reflectance targets. The targets are manufactured so that their reflectance is known and represent even steps from high to low diffuse reflectance. The response curve of the system is determined using this data. The same process is run against a calibration marker and then a set of targets representing skin tones. The targets may be manufactured to represent the reflectance of skin, or may be an area of a test subject's skin with a known measurement. The targets are chosen to represent a wide range of skin tones and color.

A color calibration response for each device is then built by transforming each device skin measure for linearity using the gray scale response curve. The response of each color is then calibrated to a white point using the calibration marker as a reference. A transform is then built for each device by mapping its adjusted color response to the known measure from the targets. The resulting device calibration may be stored on the OAPTA service process server accessible to the application. It need only be updated if there is a change in the imaging software for the device or to include a new device.

A color of a surface of the object may be measured by directing a user to place the marker in proximity to the surface of the object. Measuring a color of a surface of the object may also include interactively guiding a user to position the device image sensor and the object relative to one another to match a calibration target. The interactive guidance can include voice and/or video direction and other user cues such as vibration or sound feedback (ping tones, etc.) to let the user know that another step is needed, such as a cue that the user has drawn the device far enough from the surface to gives the best data. Measuring a color of a surface of the object can further include, upon positioning of the device image sensor at a specific distance from the marker, capturing a color of the surface of the object. Determining the surface reflectance of the object may also include transforming the captured color to a surface reflectance of the object.

A system that may be used for the for capturing of accurate color of an object for use in the methods and systems herein includes at least one computer that itself includes a memory for storing computer-executable instructions and a processing unit for executing the instructions stored in the memory. The execution of the instructions configures the computer to perform operations including calibrating a plurality of settings of a device (which can have an image sensor and/or preferably a light source) using a marker having a known size; measuring a color of each of a plurality of surfaces of the object; determining a surface reflectance of the object based on the measured colors; and determining a surface color variation of the object based on the calibrated settings, the measured surface colors, and the surface reflectance of the object. The plurality of surfaces can include regions of skin as noted above, and the device can be those mentioned above. The marker can further have a known reflectance. In its simplest form and usage, as noted herein, the marker can be a white sheet of paper with known size and known reflectance.

Calibrating the device may include directing a user to place a marker on a substantially white field (or using a white sheet of paper as a marker having a substantially white field). Calibrating the device can also include setting, based on a captured image of the substantially white field, at least one of aperture, sensitivity, exposure, exposure time, and white balance of the device. Calibrating the device can also include setting a light associated with the device image sensor to a known brightness. Further, calibrating the device can include interactively guiding a user to position the device image sensor at a specific distance from a surface of a marker. In so doing, the user will reach a point by user device interaction (a Haptic interface) wherein the device vibrates or gives another cue to the user that the device has reached its preferred distance for achieving the optimal light source brightness and focus to give the best user data collection. Moreover, calibrating the device can include, upon positioning of the device image sensor at the specific distance from the surface of the marker, locking at least one of the settings of the device. The settings of the device can be automatic exposure, automatic focus, exposure time, sensitivity and/or automatic white balance. The locked settings of the device can be applied while measuring the color of each of the surfaces of the object.

Measuring a color of a surface of the object may include directing a user to place the marker in proximity to the surface of the object. Measuring a color of a surface of the object can also include interactively guiding a user to position the device image sensor and the object relative to one another to match a calibration target. The interactive guidance can include voice direction and/or optionally video direction and/or user feedback such as vibration and/or a notification sound. Measuring a color of a surface of the object can further include, upon a positioning of the device image sensor at a specific distance from the marker, capturing a color of the surface of the object. Determining the surface reflectance of the object may include transforming the captured color to a surface reflectance of the object.

For each scan area, the information should include: color information, the amount of specular reflection; and color variation and other information as noted above. User data collection may also include user feedback information (such as to leave out or add specific ingredients). This user data collection information is then encoded into a search key as described above. The key may be associated with the user for future orders. An algorithm then performs a search on continuous n-space using the key, and returns the mix formula. The mix values are attached to the transaction. A production system is selected for the order, and the order is produced. The produced order is sent to the customer.

When the user receives the product and evaluates it, in some cases, the user may wish to change or modify the product and re-order it. To do so, the user may then follow a set of steps to modify the product. This modification of the product is an extension of the creation of a basis to provide reference OAPTA feedback. In creating the original OAPTA, the user may use various methods and systems described in the patents incorporated herein by reference above, and the various implementations of such systems and methods for specifying and formulating topical agents that are optimized for the characteristics of particular individuals using, for example, image analysis techniques applied to photographs taken with mobile phones, tablets, webcams, digital cameras, gaming consoles, televisions, virtual reality goggles, smart glasses, home assistants (such as Alexa™ or Google® Home™), which preferably have camera and light sensor requirements, and other consumer or professional devices that have an image sensor and more preferably a light source.

Optimized Aesthetic and/or Protective Topical Agent

In one implementation, a system is provided that generates a specification for a customized topical agent, referred to herein as the "Optimized Aesthetic and/or Protective Topical Agent," abbreviated herein as "OAPTA." The OAPTA is formulated for the needs and characteristics of a specific individual client, referred to herein as the "user." The OAPTA can include a set of possible components. The set can be large enough to meet most needs of a given user. In some instances, only a small number of components are used in a specific formulation of an OAPTA for a user. The OAPTA may be created to be various types of cosmetics used on the skin for either aesthetic, coverage and/or protective purposes such as foundation, make-up, skin care, sun care and other color cosmetic formulations and personal care products and should not be considered to be limiting. Therefore the application can be any customized cosmetic formulation, however, for shorthand purposes, the applicants will refer to all such customized cosmetic formulations collectively also as OAPTA. The components of the OAPTA (an OAPTA component set) can include, but are not limited to:

Topical bases, water, solvents, emulsions, gels, gums;
Moisture and humectant agents;
Ultraviolet (UV) filtering and/or sun screen active agents;
Opacity (hiding) agents;
Color control agents;
Reflectance (shine, matte, opalescence) control agents;
Anti-inflammatory agents (e.g., aloe, etc.);
Protective agents (e.g., vitamin E, etc.);
Colorants and/or dyes;
Thickeners and/or rheology agents;
Buffers and other pH adjusting agents or neutralizing agents;
Organic additives and/or fragrances; and
Preservatives and anti-fungal or anti-microbial agents The user may use a mobile device, computer or other related device as noted above. The device preferably has an ability to run an application and/or download an application, and preferably has a user interface for modifying and/or proactively requesting a separate new OAPTA after an initial OAPTA is formulated into a product. The user may login and select an order, or enter the order number. If not creating an initial OAPTA, and a user chooses to modify and/or create a new OAPTA, the user is preferably presented with an interface to modify the order. However, it should be understood that variations of the system could involve use of a voice-only device having voice command actions through user-assisted voice or word prompts which can incorporate access to a user help service if needed.

Referring to FIG. 1, in one example, an initial OAPTA is provided to the user using the following high-level steps. For the sake of brevity and clarity, the aggregation of all the steps to provide an OAPTA to a user will be referred to as a "service" herein. In Step 102, the user is identified using, for example, a user name and password that provides access to the present system. Other log-in methods and/or security steps may, of course, be implemented, including log-in confirmation identifiers (such as text confirmation numbers, photo identifiers, finger print, retina security) and the like. In the case that the user has not previously used the system, the user can proceed to registration to set up a new account (Step 104). The user's details (e.g., name, address, etc.) can then be stored in user database 150. Once the user is identified by the system (e.g., logged in), data can be collected (Step 106) to determine the user's needs and preferences (e.g., allow the user to indicate desired cosmetics, indicate preferred brands or products previously used, allow the user to specify any allergies, capture skin imagery, and so on). The interface may provide prompts to the user to complete an initial survey and question and answer prompts can assist in providing the desired data. The data collection step can also be performed using a professional service, such as an in-person professional consultation (Step 108) or, alternatively, and preferably can be performed by users themselves by taking a photograph using an application on a consumer device (e.g., a mobile phone, tablet, digital camera, or other device as noted herein) (Step 110), which will then automatically validate the photograph for color accuracy, quality, and other properties (Step 112). Information captured by the professional service and/or the device application can be stored in the user database 150 for later reference and reuse.

Following data collection (or reference to previously collected data), Step 114 provides for the OAPTA specification, in which the components of the OAPTA are specified using components such as those described above. In Step 116, based on the OAPTA specification, the instructions to formulate and/or manufacture the OAPTA are generated. If the user is using an application to generate the OAPTA, the application can display the custom product to be created (Step 118), and allow the user to place the product in a shopping cart (Step 120) and purchase it (Step 122). The generated formulation instructions can then be used to compound the OAPTA or select a premade OAPTA that matches the formula (Step 124). The OAPTA can then be delivered to the user (Step 126), and feedback can optionally be collected to determine if the User's need(s) were met (STEP 128).

OAPTA System

In one implementation, the system 200 that provides the OAPTA to users is made up of a set of components and services. The system 200 can include a shared OAPTA component set 210, such as that described above, for use by the various OAPTA services in the system 200. At least one OAPTA reference service 220 can facilitate the creation of an OAPTA for a collection of reference uses and the assembly of OAPTA metadata 230. The OAPTA reference service 220 collects user data in the same manner as the OAPTA production service 240, and can collect additional user data to formulate an optimal initial OAPTA specification.

The OAPTA Metadata 230 is the assembly of user data collected from an OAPTA reference service 220 in a form that allows for the mapping of user data collected from the OAPTA production service 240 to the OAPTA specifications generated by the OAPTA reference service 220. At least one OAPTA production service 240 provides for the creation of the OAPTA specification using the OAPTA metadata 230 generated by at least one OAPTA reference service 220.

OAPTA system feedback 250 provides for the collection of OAPTA feedback from at least one OAPTA reference service 220 and at least one OAPTA production service 240, in order to modify or change an OAPTA component set 210 and/or modify the specification, formulation and/or compounding 260 of the OAPTA production service 240.

Shared OAPTA Component Set

The shared OAPTA component set 210 can be specified as described below; yet it is to be appreciated that the shared OAPTA component set 210 can be specified in various suitable manners that function similarly within the OAPTA system described herein. A group composed of a dermatologist, an esthetician, and a cosmetic colorist is referred to herein as an example of an "OAPTA professional group." In one implementation, the shared OAPTA component set 210 is specified by an OAPTA professional group. The shared OAPTA component set 210 can be specified first as a full set, and then as a set of connections indicating those components that can be used with one another. For instance, a set of colorants can be specified as only usable with a specific topical base, or a group of components that work together to provide more opacity can be indicated as most effective when used together. Similarly, groups of those items which are best for users with certain allergies or skin conditions can be identified and tagged.

This initial mapping of components provides data for the specification method of the OAPTA production service 240, and will be referred to herein as "specification hints." In one embodiment herein, the specification hints are represented as a non-directed graph, which is converted to a set of minimum spanning trees. It is to be appreciated that it is faster to traverse a minimum spanning tree to discover which components can be used together, rather than evaluating a non-directed graph. After this conversion, a single item in the shared OAPTA component set 210 can be referenced by multiple spanning trees which compose the specification hints. After initial creation, the specification hints can be updated or discovered by OAPTA system feedback 250, as well as modified by the OAPTA professional group.

OAPTA Reference Service

The OAPTA reference service 220 can be constructed after the shared OAPTA component set 210 is specified. The OAPTA reference service 220 produces the OAPTA metadata 230 needed to construct the OAPTA production service 240. In one example embodiment, the OAPTA reference service 220 is configured as a professional service. In another implementation, the OAPTA reference service 220 is configured as an online business and a retail store. The implementation of the OAPTA reference service 220 as a professional service is used as an example in the description below.

Reference User Identity

As a professional service, the OAPTA reference service 220 can use best practices for managing a user identity. In addition to this, it can also implement a privacy policy and information use policy that allows the reference service 220 to collect and store user data in a form that is anonymous and does not identify the user, and that can be used to build OAPTA metadata 230. Agreements can also be made, based on some consideration, for the data to be used by the OAPTA system 200 so that a user of the production component of the system 200 can identify a specific reference user (such as a celebrity) that has a similar OAPTA product need.

Reference User Data Collection

The OAPTA reference service 220 can use the same data collection as the OAPTA production service 240. In addition, this data can be augmented with data collection methods as specified by the OAPTA professional group.

Common Service Data Collection

In one embodiment, the service data collection uses an application on a set of mobile devices that have similar features and are manufactured in a manner to have similar information gathering and media display properties. The mobile application can walk the user through a series of steps to collect the data. For example, the application can ask the user if he or she has specific needs, allergies or a skin condition of concern. The application can show a video instructing the user as to which step to perform next, and/or can use the context of a mobile game to obtain and optimize the data. The mobile device can be selected, and the application constructed, to provide consistent data from each collection. Consistent image data collection can be performed using one or more of the following methods.

1. In one example, a manufactured token or marker with known characteristics (e.g., a portion of a new dollar bill, a new quarter, a piece of white paper, or a marker which is manufactured and sent to the user) is used. A mobile device application (or other device application) can instruct the user to take a picture of a portion of the marker alone and/or, if applicable, the marker next to the user's skin. The image is sent to the OAPTA Service, where it is calibrated based on the marker used, and the necessary data is generated from the image.

2. In another example, a reference color chart is projected on the user device screen and the user is instructed to take a picture in the mirror capturing both his or her skin and the reference color chart in the same frame. The image is sent to the OAPTA service, where it is calibrated based on the marker used, and the necessary data is generated from the image.

3. In a further data collection example, a mobile device's internal flash (or LED torch) is used as a light source, and the user is instructed to take one or more picture(s) of his or her skin in a specific manner. The image is sent to the OAPTA service, where it is calibrated based on the flash and Exif data from the device, including focal length, and the necessary data is generated from the image.

4. In another example, packaging used to ship OAPTA products is designed in a manner to hold a mobile device to provide a light shield and define a specific distance from the user's skin. The user is instructed to take one or more picture(s) of his or her skin in a specific manner. The image is sent to the OAPTA data collection service, where it is calibrated based on the flash and Exif data from the device, including focal length, and the necessary data is generated from the image.

5. In another, and preferred, example, an image can be captured by an application on a mobile device that allows software to control the camera. The software running on the device can set the device to use only a flash or light resident on the device, such as the LED torch and/or it can also use facial detection on the device to time when an image is taken. The image can be taken when, for example, the distance to the user's face is within a known distance and/or the user's face is centered and in focus. The software running on a mobile device can also use real-time video capture to determine the amount of ambient light (not using the flash) and can use a voice, text, sound or effect prompt to interactively suggest to the user how to change the lighting. Information about the ambient lighting detected in video mode before the digital photo is taken with the flash can be sent along with the image for processing. Additionally, two images can be taken in quick succession, one with ambient light and one with flash.

Capturing accurate skin color using the camera and a light source on a device having an image sensor, such as a mobile smart phone with an LED torch will now be described in further detail. It is to be appreciated that, although the present techniques are described primarily with respect to capturing accurate skin color, other applications are possible, particularly in circumstances where one would use a colorimeter.

Figure 3A:
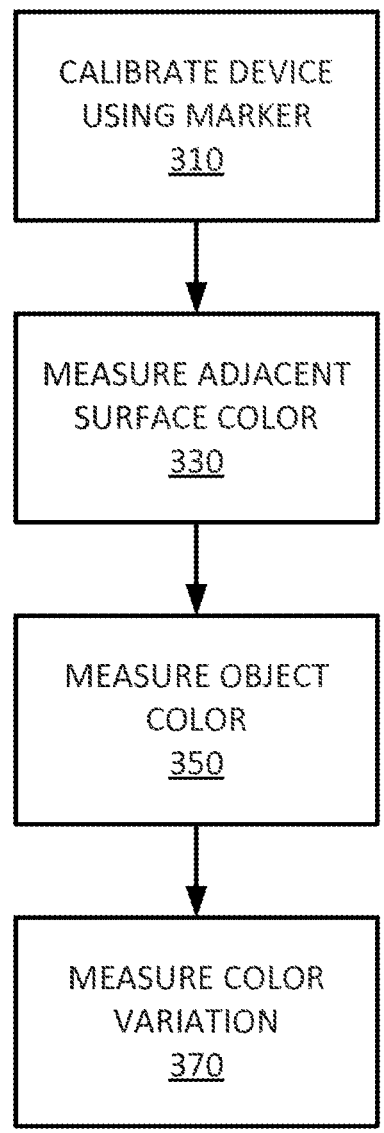
FIGS. 3A-3D are flowcharts of example methods for capturing skin color using a device with an image sensor for use in the invention.

FIG. 3A depicts one implementation of a process for capturing skin color using a mobile device or other device with an image sensor. In Step 310, the device is calibrated using a marker of known size on a white or substantially white field, wherein the marker may itself be a white field, such as a standard sized sheet of paper as noted above. In Step 330, the system measures the color of an object's surface (e.g., a skin region) adjacent to the marker. In Step 350, the color of an object of known size is measured and, in Step 370, the system measures the color variation of an object's surface based on the luminance found in Step 330 and/or Step 350.

Figure 3B:
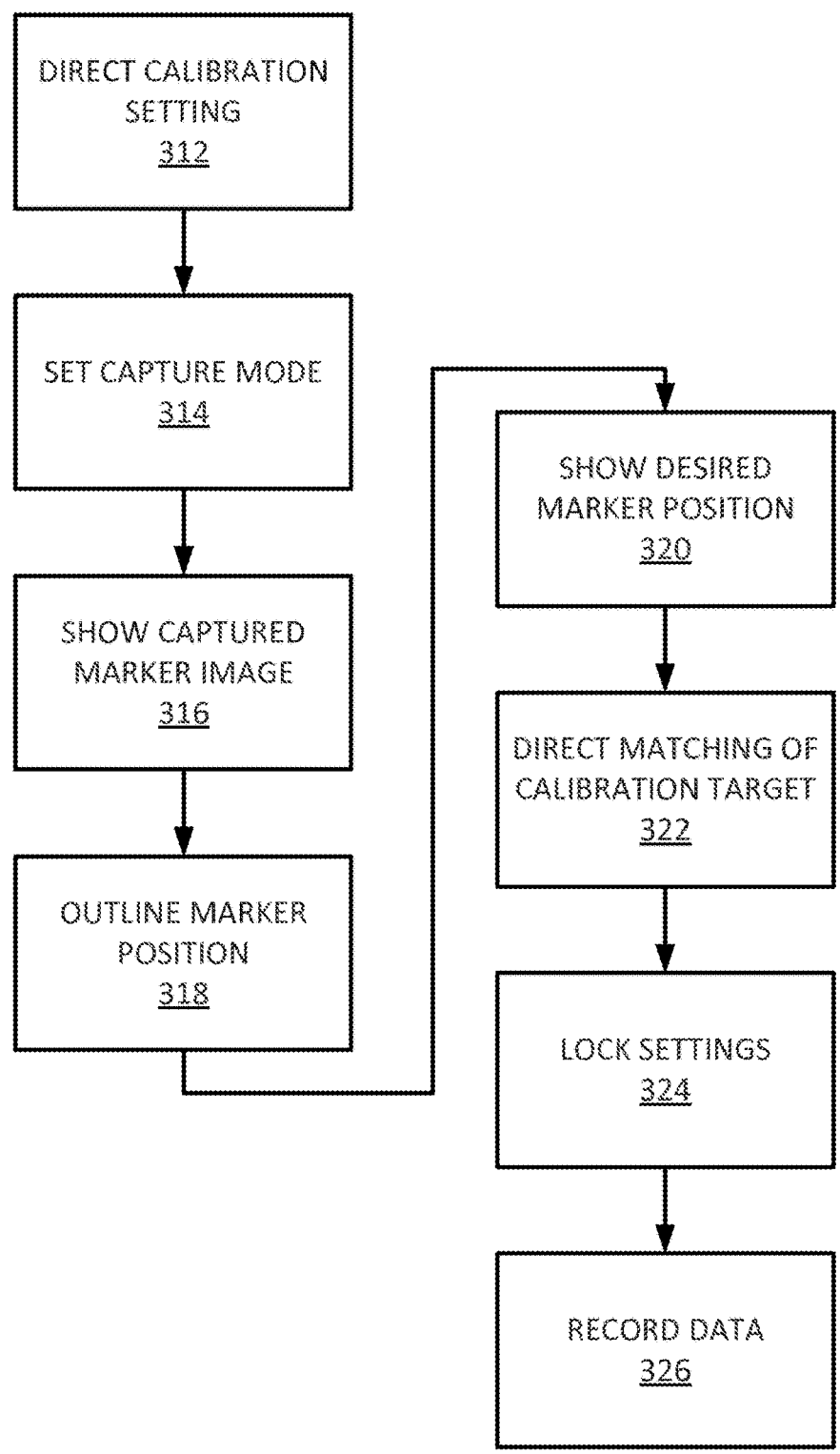

Referring now to FIG. 3B, the device calibration Step 310 is shown in further detail. In some implementations, calibrating the device requires a setting where a software detectable object of known size and known reflectance (a "marker") is placed on a white or substantially white field or a marker is used that is a white field (such as a particular sheet of paper) that has known size and reflectance. This setting and the object can be manufactured, and/or can be, for instance, a portion of product packaging, or included within a packaged product, such as a skin care product. Alternatively, this setting can be created by placing a common object or any other object having well-known properties, such a coin, on a white field or substantially white field with known properties, such as two sheets of copier/printer paper or simply using a white sheet of paper as a marker that is a white field having known size and reflectance properties. The distance used for calibration can be determined to be close enough to the measured surface to reduce the effect of ambient light.

In Step 312, a software application on the device preferably directs the user to set, place or construct the setting used for calibration. The software can set a specific video or image capture mode for a camera on the device, and set the light associated with the camera to a known brightness (Step 314). The software on the device can interactively show the captured image of the marker on the field (Step 316), and can detect the marker and highlight and/or outline the marker's position and/or the marker properties for the user (Step 318). In some implementations, the marker's position may be offset so that the software uses the white field to set desired device settings such as the aperture, sensitivity, exposure time, and white balance of the device.

In Step 320, the software preferably shows and/or highlights the desired size and/or position for the marker that will result in the device's camera being positioned at a specific distance. This size and position is referred to herein as the "calibration target." The software can interactively direct the user to match the highlighted marker with the calibration target (Step 322). When the user positions the device to match the marker with the calibration target, the software can cause the device to lock automatic exposure, automatic focus, sensitivity, exposure time and automatic white balance (Step 324). This locking effectively calibrates aperture, sensitivity, exposure time, shutter speed, focus, and white balance to a predetermined distance to a surface with known reflectance. The white point (and other data) of the setting can be recorded and used to calibrate subsequent sessions (Step 326).

Figure 3C:
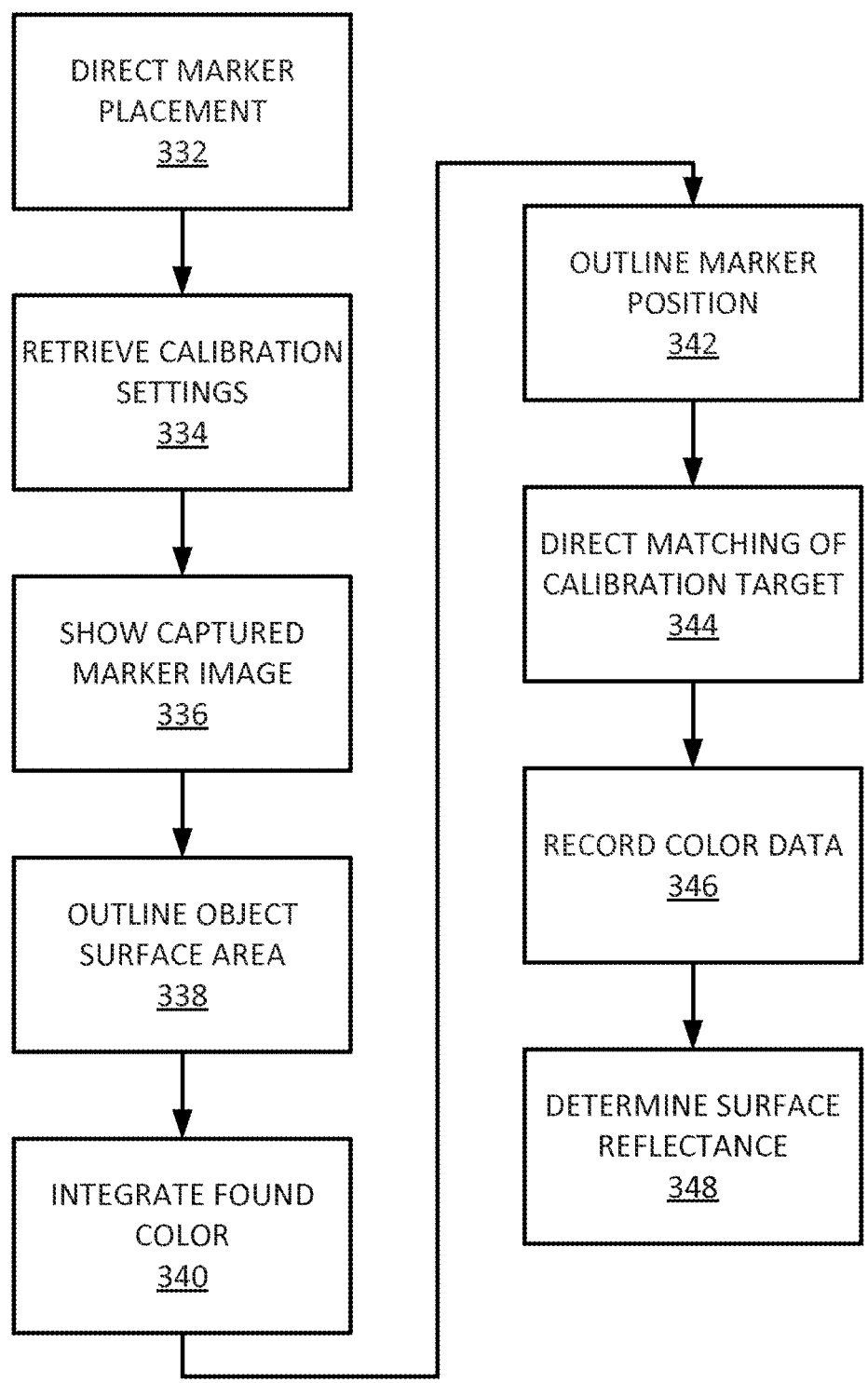

Referring now to FIG. 3C, an optional adjacent surface color measurement Step 330 is shown in further detail. In one embodiment, measuring the color of an object necessitates that the distance from the device's camera to the surface of the object's surface be set, or at least known. If the object size is not fixed, this can be done by placing a marker of the same size used in the calibration step adjacent to the surface to be measured.

In Step 332, the software on the device may direct the user to place the marker adjacent to or on the surface to be measured. In Step 334, the software preferably maintains or recreates the locked settings from the calibration step 310. The software can optionally interactively show the captured image of the marker adjacent to the object (Step 336) (or alternatively, just the capture image of the marker), including showing an outline of the area of the object's surface being integrated and measured if applicable (i.e., the "swatch") (Step 338). In Step 340, the software can integrate the color found in the swatch and show the found color interactively. The software can also detect the marker and highlight or outline the marker's position for the user interactively (Step 342). The marker's position can be offset so that the swatch matches the region of the captured image used to calibrate the white point.

In Step 344, the software interactively directs the user to match the highlighted marker with the calibration target. When the user positions the device to match the marker with the calibration target, the software can record the integrated color of the swatch as the raw color value of the object (Step 346). The software can use known techniques to apply the found white balance and stored data about the characteristic of the device to transform the found raw color value of the object to the surface reflectance of the object (Step 348).

Figure 3D:
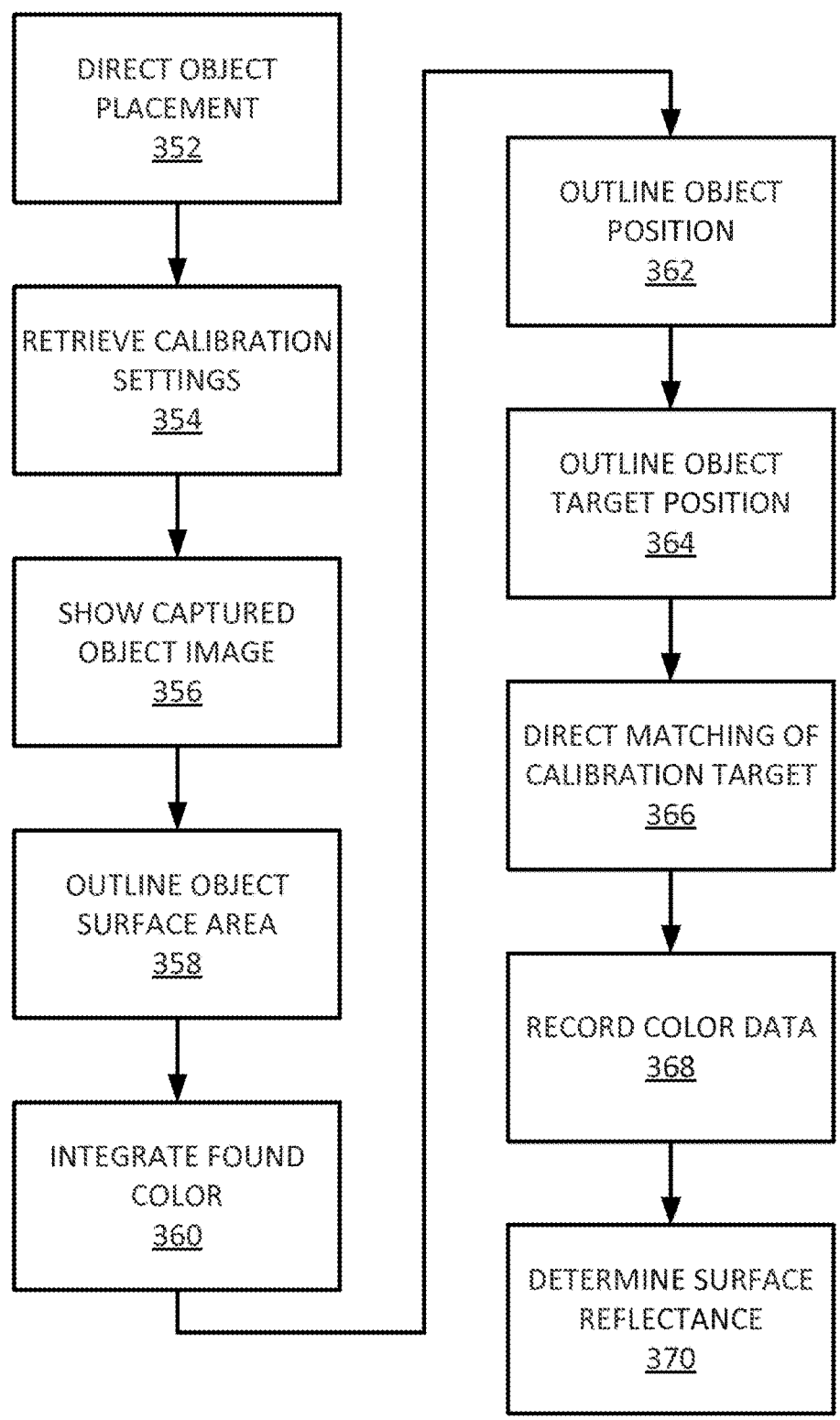

Referring now to FIG. 3D, the object color measurement Step 350 is shown in further detail. If the object to be measured has a known size, or features of a known size, the size of these features can be used to determine the distance of the device's camera to the object to be measured. For instance, in measuring skin color, the width of a user's wrist, or the distance between the user's pupils can be used to detect the distance of the device's camera to the user's skin.

In Step 352, the software on the device directs the user to point the camera at the object (e.g., wrist, face, right and left cheeks, forehead, right and left jaw or other skin region), and to hold the object in a position to match an outline on the display. In Step 354, the software maintains or recreates the locked settings from the calibration step 310. The software can interactively show the captured image of the wrist or other object, and highlight the found width of the wrist (Step 356). The software can further show an outline of the area of the object's surface being integrated and measured (i.e., the swatch) (Step 358). In Step 360, the software can integrate the color found in the swatch and show the found color to the user interactively.

The software can also function to detect the marker and highlight or outline the wrist's position for the user interactively (Step 362), and can also interactively highlight or outline the wrist's target position for matching the calibration distance (Step 364). The software can further interactively direct the user to match the highlighted marker with the calibration target (Step 366). When the user positions the device to match the wrist with the wrist's target, the software can record the integrated color of the swatch as the raw color value of the wrist (Step 368). In Step 370, the software can use known techniques to apply the found white balance and stored data about the characteristic of the device to transform the found raw color value of the wrist to the surface reflectance of the object.

Referring back now to Step 370 in FIG. 3A, an object's surface color variation can be measured when the overall reflectance of the object is known, the device has been calibrated, and the color of a portion of the object is known. For instance, if the color of a person's inside and outside wrist is known, and the color of a person's forehead is detected using intra pupillary distance, variation in skin tone can be measured by positioning the device such that the integrated reflectance matches a known value.

Facial Region Detection

Figure 4A:
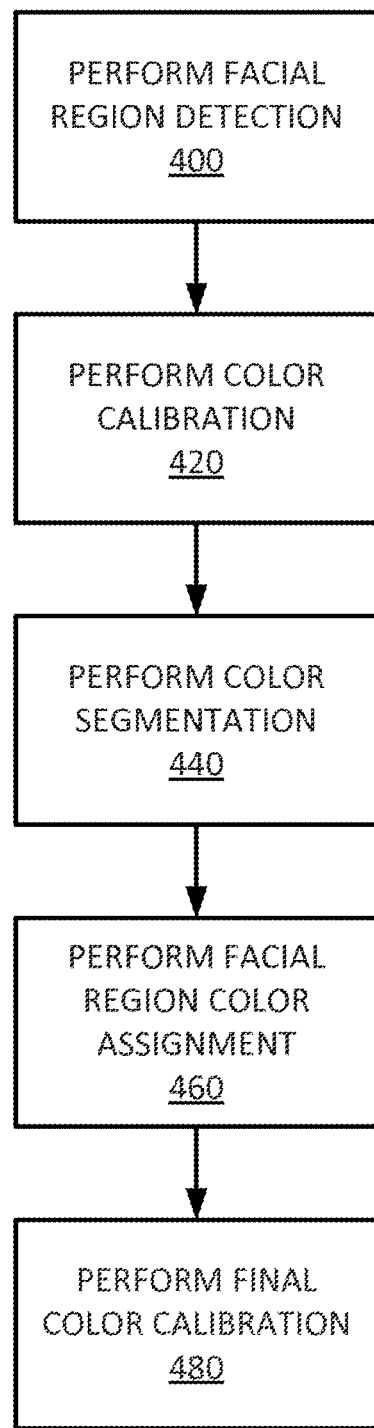
FIGS. 4A-4E are flowcharts of example methods for analyzing an image containing a facial region which may be used by a user in the invention.

In one example embodiment, the present system performs processing on an image containing a user's face or a portion of the user's face as part of formulating a customized topical agent for the user. As shown in FIG. 4A, facial region detection is performed on the image (Step 400), and calibrated color and reflectance information is provided (Step 420). Color segmentation (Step 440), facial region color assignment (Step 460), and final facial region color calibration (Step 480) can also be performed, as further described below.

In some embodiments, once an image is received by the OAPTA data collection service, it is processed to provide calibrated color and reflectance information. To assist in the calibration process, a facial region detection process (Step 400) can be used. For example, open source and other techniques exist, such as use of facial recognition software as noted hereinabove, to detect the position of the face, eyes, mouth and nose in a digital photo. For a further reference, a Haar Cascade Classifier can be used with training sets built for detecting facial features. One software package and associated training sets that can be used to provide this functionality is found at OpenCV (opencv.org). Additional software and facial recognition processes such as those of Giaran, Inc. may also be used Using the positions of the facial features determined by a suitable procedure such as those described above, existing open source and other techniques or available software can be used to detect the position of discrete facial features in the digital photo. For reference, active shape models developed with a large training set can be used. One software package and associated data that can be used to prove this functionality is the stasm library (which is an open source facial feature detection library), the Apple X 3-d modeling software, ARKit, or the software and systems available from Giaran, Inc. and/or described in U.S. Patent Publication No. 2017/0076474A1. All of the above noted device setting and/or facial recognition software may be used to locate and model the correct color and related user data.

Figure 4B:
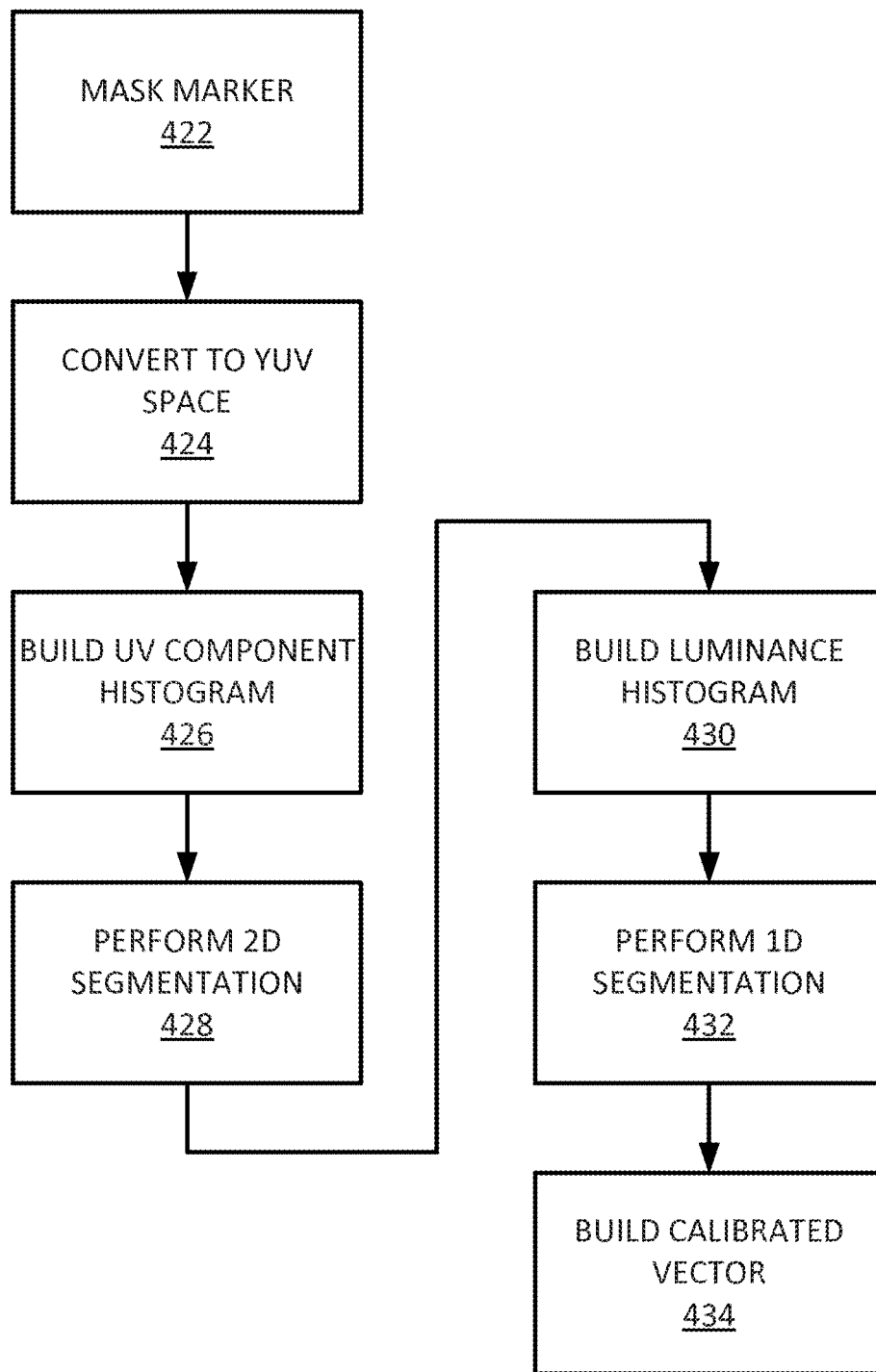

The discrete facial feature points determined above can then be assembled into a set of polygonal regions. In one implementation, the face includes 77 recognized feature points, although any suitable number of feature points and regions can be used. The recognized regions can include some or all of, but are not limited to:

Full face (includes all regions);
Forehead;
Right cheek;
Left cheek;
Nose;
Nose bridge;
Mouth (includes both lips);
Chin;
Right eyebrow;
Left eyebrow:
Right eye;
Left eye;
Top lip;
Bottom lip;
Right jaw line; and/or
Left jaw line;
Color Calibration FIG. 4B depicts Step 420 in further detail, namely, one way to employ a method to provide calibrated color and reflectance information using a captured image. In Step 422, the image is calibration, and the marker, if used, is recognized and masked. The image is converted into YUV color space (Step 424) and a 2D histogram of the UV image components is built (Step 426). In the following Step 428, 2D segmentation is performed on the UV histogram to find a set of colors representing highlight, body color and spot color. A luminance histogram of the Y image component is built (Step 430), and 1D segmentation is performed on the luminance histogram to find, e.g., a luminance set representing reflectance of body color, amplitude of highlight reflection (shininess) and shadow luminance (Step 432). Then, in Step 434, a calibrated n-dimensional vector is built using the combined UV and luminance sets. This vector is referred to hereinafter as the "nColorVector." Of note, the nColorVector can contain data representing skin shininess and color variation (spottedness).

In another example method, a digital photo can be calibrated based at least in part on data embedded in a digital photograph, such as the IFD tags found in JPEG compression, or Exchangeable Image File format (Exif) data. The characteristics of the device used to take the photograph can be used to pre-calibrate the color. The distance from the camera to the user's face can be determined by the inter-ocular distance found by facial feature detection, such as that described herein above. The shot data embedded in the digital photo, such as brightness, flash characteristics, and so on, can be combined with the distance from the camera to adjust the luminance of the image. Further, additional data sent by software resident on the device at the time of the shot, such as ambient lighting information or an ambient lighting image, can be used to color correct for ambient lighting.

Color Segmentation

Figure 4C:
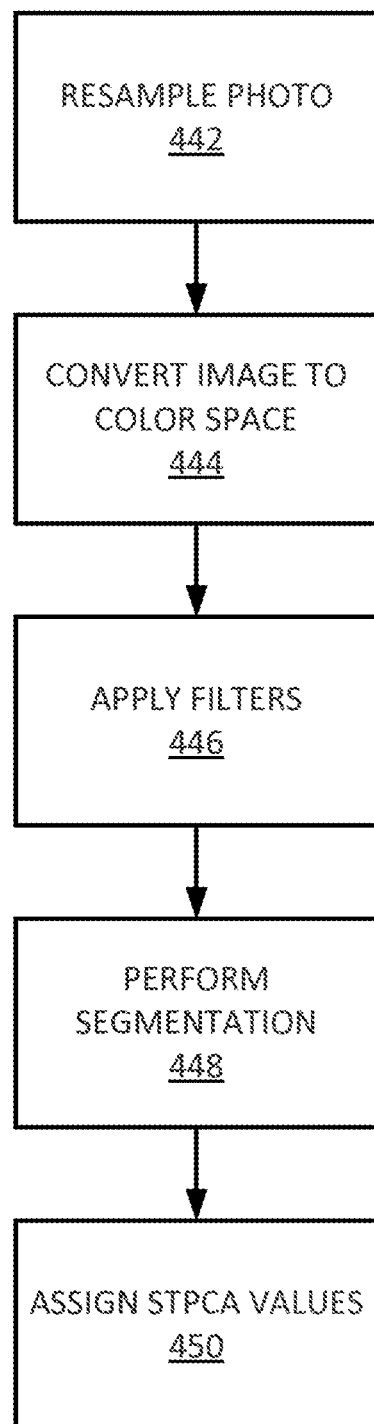

Another way to create color segmentation is as part of the processing of the digital photo. One way to perform color segmentation (Step 440) is shown in FIG. 4C. In Step 442, the digital photo is resampled to a smaller size that matches the resolution needed for identifying skin tones. The size can be determined by the dimensions of key facial regions. For instance, the size can be calculated as newSampleHeight= (Image.height*128)/sqrt(Area of Face region in Pixels). This resampled photo is referred to hereinafter as the "segmentation image."

The segmentation image can be converted to a color space using, for example, a 3×3 matrix transform that transforms skin color from an RGB representation to a skin tone principal component representation (Step 444). The skin tone principal component space will be referred to herein as "STPCA." This transform can be found by performing principal component analysis on a large array of RGB colors of skin tones from digital photos taken by various users with matching devices (e.g., associated by being taken by a particular mobile phone). This image will be referred to as the "PCA segmentation image." Principal component analysis is a well-known method of reducing the dimensionality of a set of vectors.

The principal component channel (channel 0) of the PCA segmentation image is prepared for segmentation by applying additional filtering, such as a bandpass filter (Step 446). In Step 448, segmentation can be performed by using well-known techniques such as a Watershed transform. The resulting image is referred to herein as the "segmentation label image." The brightest pixel of the PCA segmentation image channel 0 within each segmentation label image region can then be used to assign an STPCA value to each segmentation label region (Step 450).

Facial Region Color Assignment

Figure 4D:
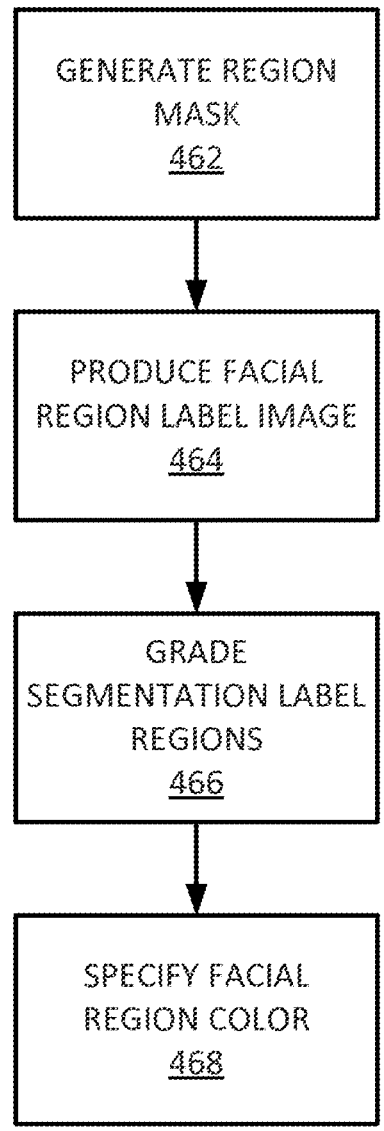

Referring now to FIG. 4D, given the delineation of a facial region, one procedure for determining the skin tone for a region (i.e., Step 460) is as follows. In Step 462, a region mask is generated for the facial region by, for example, drawing the region as a white polygon on a black background. The segmentation label image produced by the color segmentation process described above is masked by the region mask to produce a "facial region label image" (Step 464). Then, in Step 466, the segmentation label regions in the facial region label image are graded by area and by maximizing the distance of the label region's assigned STPCA value from STPCA values representing shadow and specular highlight. The STPCA value for the segmentation label region with the best grade is then specified as the "facial region color" (Step 468).

Final Facial Region Color Calibration and Additional Data

Figure 4E:
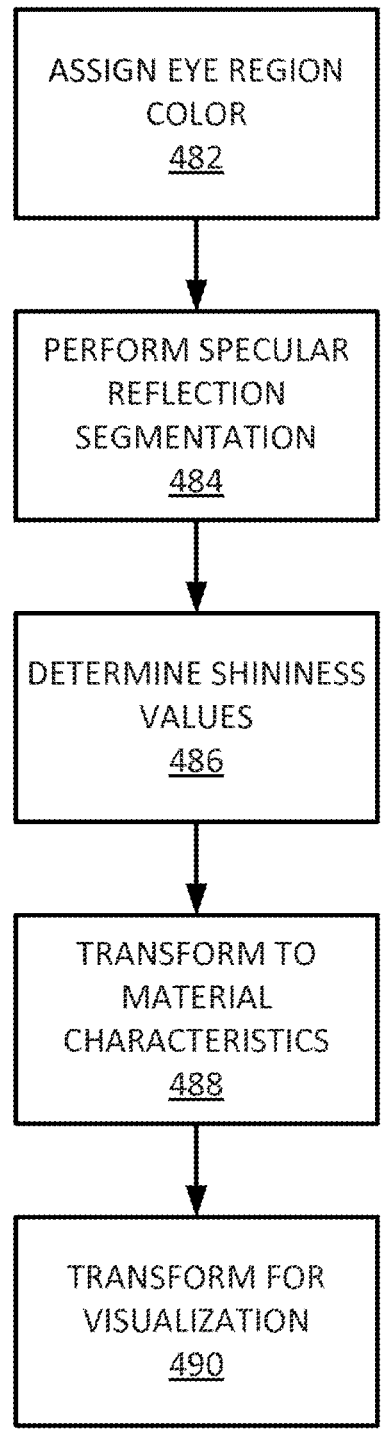

Final facial region color calibration (Step 480) can be performed using the following steps, as shown in FIG. 4E. In Step 482, a facial region color for the eyes may be determined and assigned and, in particular, a grey level for the sclera of the eye determined. In Step 484, segmentation of specular reflection in the eye regions can be used to determine if the flash and/or a torch were fired and if other point sources of light were present (see further description below). Specular reflection sub-regions are detected for each facial region, and a "shininess" value is determined for each facial region based on its size relative to the overall region size (Step 486). The shininess metric for the eyes can also be used to calibrate other regions.

Final transformation of STPCA values, grey level, and shininess values can be transformed directly into material characteristics used for manufacturing of a cosmetic product, rather than an intermediate form (Step 488). Further, transformation of STPCA into RGB or LAB color spaces can be performed for visualization for the user. These can be performed using a modified version of the original PCA matrix, adjusted by the grey level and shininess value.

As mentioned above, facial region color calibration can involve determining the presence and color of lighting sources (other than known sources, such as a camera flash or LED torch) based on an evaluation of specular reflection in the eye regions. In one implementation, this process includes the following steps:

Subtract the red channel from the digital photograph. Take a bandpass filter of a relatively small number of pixels in the high frequency (e.g., around two pixels), and a higher number of pixels in the low frequency (e.g., around five or six pixels) to remove detail. Perform a histogram on the result and take a threshold at the 99th percent of the pixel population that the histogram has, thereby determining all of the highest lights. Dilate the highest lights by approximately twenty pixels to create a mask for the lights. Apply another bandpass filter to the resulting image at a high frequency of approximately ten pixels and a low frequency of approximately twenty pixels, resulting in an image having broader features, including pulling out the iris of the eye. Dilate the dark part of the eye by approximately ten pixels, resulting in the intersection of the inverse of the iris, or the dark part of the eye, with the discovered highlights. Threshold the bright spots (i.e., reflections of light) within the eye with the initial inputs. Use the resulting spots to mask the original color of the input images and determine if there are previously unknown light sources. Subtract any discovered unknown light sources and color calibrate.

User Data Collection Specific to the Reference Service

The common service data collection can be augmented by additional data collection which aids the OAPTA professional group in the reference OAPTA specification. In one implementation, this data includes one or more of:

Visible, IR, and UV color spectrographic data;
Bidirectional reflectance data;
Photomicrographs of specific facial skin sites (and evaluating skin health);
Analysis of surface skin oils or residue using a Raman Spectrophotometer, Mass Spectrophotometer, or other instrument; and/or
Augmented data provided by the common service data collection by interview.

Reference OAPTA Specification

The OAPTA professional group can specify the components and amounts to be used in making a custom OAPTA for a user based on the reference user data collection. The specification and the reference user data can be compiled to create an entry in the OAPTA metadata 230.

Reference OAPTA Formulation

The OAPTA professional group can provide a set of instructions that specify the order and methods that are used to combine the components to make the OAPTA product. This set of instructions can be added to the current entry in the OAPTA metadata 230.

Reference OAPTA Compounding

In one implementation, the OAPTA product is compounded manually based on the OAPTA formulation 260. In another method of compounding, a review of the formulation instructions and the shared OAPTA component set 210 is used in an apparatus which will automatically compound the OAPTA product based on the formulation instructions. An exemplary device is described in detail in the applicant's co-pending application Ser. No. 15/855,064, incorporated in relevant part for compounding an creating a OAPTA product and further for delivery of such product. However, other suitable mixing and blending apparatuses as are known in the art, preferably that are programmable and responsive to an electronic and/or digital control system are preferred.

Reference OAPTA Delivery

The OAPTA product may be delivered on premises to the user at a service location after being compounded in the same or a different location and during the user's use of the system. The OAPTA product after compounding in the same or a different location from a point of service can be directly given to or shipped to the user.

Reference OAPTA Collection

Reference OAPTA collection may be accomplished through billing via the professional service. Further, payment information may be collected as part of the common service data collection, and payment may be collected on OAPTA delivery and/or at the time of ordering through various on-line payment methods as are known in the art, preferably a secure payment service and/or shopping cart feature.

Reference OAPTA Feedback

User feedback may be collected through an interview after the OAPTA product is delivered and tested. Feedback information may also be collected by the mobile application used for common service data collection.

OAPTA Metadata

The OAPTA metadata 230 may include one or more of the following example data fields, including user data collection, although other fields as desired for forming an OAPTA may be provided or used:

Common service data;
User ID;
Geographic Region;
Gender;
Birthday;
Date;

Combined Vector;
Ultraviolet radiation exposure;
Allergy vector;
nColorVector;
Reference specific data;
Skin color spectra;
Bidirectional reflectance data;
Photomicrographs of specific facial skin sites;
Skin surface oil index;
Reference specification;
Reference formulation instructions;
User device operating system;
User device software information;
User beauty profile (color, shininess and/or opacity); and/or
Tags for spanning trees found in the specification hints.

The data noted above may be captured through scanning, user self-reporting, such as through a survey or query, self-reported data from onboarding data gleaned from device sensors (e.g., GPS) and data captured through social media sites.

CombinedVector can be thought of as a point in n-space. The magnitude of each component is normalized to its significance system-wide.

Reference data can include one or more ground truth data sets that include defined values relating to, e.g., skin color, reflectance, allergies, and/or other data as described herein, for which known OAPTAs can be accurately formulated. In other words, for a specific set of values in the ground truth data set, there can be a predefined topical agent that is optimized for those values. The predefined topical agent can also be similar to or the same as an existing product, such as a commercial offering of the OAPTA's compounding company or any third party's commercial product. Thus, one way to determine an optimal OAPTA for a user can be to determine the relative proximities of the user's captured skin data with the ground truth data set values, and select the data set values that are closest in proximity. The OAPTA or existing product corresponding to those closest values can then be the unique compound selected for the user.

OAPTA Production Service

The OAPTA production service 240 can be constructed after a sufficient number of records have been collected into the OAPTA metadata 230, and the reference service OAPTA compounding means have been automated.

Production User Identity

The OAPTA production service 240 creates and begins to manage a user identity when a user purchases software, e.g., a mobile application and launches the application for the first time. The service creates a data store to hold user data, and provides for retrieval of the data based on the user identity. The user identity can also contain shipping and billing information.

Production User Data Collection

The OAPTA production service 240 can use the common service data collection previously described for the OAPTA reference service 220. The user's common service data for a given session is stored with the production user identity.

Production OAPTA Specification and Formulation

The OAPTA production service 240 uses the OAPTA metadata 230 generated by the OAPTA reference service 220 to synthesize a specification. For example, based on the facial image data gathered and processed as described above, a particular user's complexion can be matched to an existing reference complexion for which a cosmetic formulation has already been defined (e.g., based on an actual reference user, a ground truth data set, etc.). Properties unique to the user, such as allergies, can be considered in determining whether a particular formulation will be compatible with the user. New formulations derived by the system can be saved as references for future use.

In one implementation, to process and order an OAPTA product, the system obtains the user's current common service data that is linked to the user's production user identity, and determines the closest match to the common service data combined vector in the OAPTA metadata 230 as described above. If the distance between the combined vector and the closest match is too far, the user can be queried if he or she would like to be promoted to being a reference user and end the current order.

The system can then locate the next closest match filtered by the first match's spanning tree tags, and can use geometric algebra or singular value decomposition to find a third filtered match point describing a hyperplane. If the distance between the combined vector and the surface of the hyperplane is too large, the user can be queried if he or she would like to be promoted to being a reference user and end the current order. For each found reference point, the blend values are determined, and a specification is built by adding blends for each component common to the closest match. Finally, the formulation from the closest match's OAPTA metadata is selected as the formulation suited to the user. Thus, an initial OAPTA and initial customized cosmetic formulation is created.

Production OAPTA Compounding

The system can use the automated compounding method specified by an implementation of the OAPTA reference service 220 described herein. In one embodiment, this is a shared resource. Alternatively, there may be multiple locations with similar automation equipment, and the location closest to the user's geographic location is chosen.

The OAPTA product can be compounded on demand after the user has proceeded through the steps described herein that allow an initial customized cosmetic formulation to be determined. Additionally or alternatively, OAPTA products can be compounded in advance (e.g., the most common formulations can be compounded and stocked) to provide for a faster turnaround time from formulation to delivery. In some embodiments, the formulation determined by the system is mapped to existing products from other vendors and brands. For instance, based on the formulation, ingredients, color, and/or other known properties of other products, the system can compare the user's customized cosmetic formulation with the other products and determine those that are most similar to or that meet a threshold of similarity (e.g., 75%, 80%, 90%, and so on). As one example, the system can determine that the user's foundation is an 88% match to an Armani foundation and an 82% match to a L'Oreal foundation. The system can also display the other matched products to the user and allow the user to purchase them in addition to or as an alternative to the user's customized formulation, thereby allowing the user the option of a close match to a commercial product for purchase or a customized cosmetic formulation based on OAPTA that should ultimately be at least as close or closer to the desired match for the user..

Production OAPTA Delivery, Collection, and Feedback

The OAPTA product can be shipped to the user from an automated compounding location, a warehouse, a retail establishment, or other location where OAPTA products can be compounded and/or stored. The user can be billed upon shipment using the production user identity information available to the system. In one implementation, the user is able to provide feedback and other data using a mobile application which serves the common service data collection.

OAPTA System Feedback

In one implementation, the OAPTA system 200 is configured to facilitate review of production OAPTA feedback 250 and compare any critical feedback to gaps in OAPTA metadata's 230 common service data combined vector space. The system 200 can adjust the allowable maximum distance from a solution if the space is too sparse, and upgrade production users to reference users to fill gaps in the model.

Implementations of the OAPTA system 200 can use appropriate hardware or software; for example, the OAPTA system 200 can execute on a system capable of running an operating system such as the Microsoft Windows® operating systems, the Apple OS X® operating systems, the Apple iOS® platform, the Google Android™ platform, the Linux® operating system and other variants of UNIX® operating systems, and the like.

Some or all of the described functionality can be implemented in software and/or hardware on a user device. A user device can include, but is not limited to, smart phones, smart watches, smart glasses, tablet computers, portable computers, televisions, gaming devices, music players, mobile telephones, virtual reality goggles, laptops, palmtops, smart or dumb terminals, network computers, personal digital assistants, home assistants (such as Alexa™ or Google® Home™), which preferably have camera, wireless devices, information appliances, workstations, minicomputers, mainframe computers, or other computing devices, that is operated as a general purpose computer or a special purpose hardware device that can execute the functionality described herein. The software, for example, can be implemented on a general purpose computing device in the form of a computer including a processing unit, a system memory, and a system bus that couples various system components including the system memory to the processing unit.

Additionally or alternatively, some or all of the functionality can be performed remotely, in the cloud, or via software-as-a-service. For example, matching functions can be performed on one or more remote servers or other devices as described above that communicate with the user devices. The remote functionality can execute on server class computers that have sufficient memory, data storage, and processing power and that run a server class operating system (e.g., Oracle® Solaris®, GNU/Linux®, and the Microsoft® Windows® family of operating systems).

The systems can include a plurality of software processing modules stored in a memory and executed on a processor. By way of illustration, the program modules can be in the form of one or more suitable programming languages, which are converted to machine language or object code to allow the processor or processors to execute the instructions. The software can be in the form of a standalone application, implemented in a suitable programming language or framework.

Method steps of the techniques described herein can be performed by one or more programmable processors executing one or more computer programs to perform functions by operating on input data and generating output. Method steps can also be performed by, and apparatus can be implemented as, special purpose logic circuitry, e.g., an FPGA (field programmable gate array) or an ASIC (application-specific integrated circuit). Modules can refer to portions of the computer program and/or the processor/special circuitry that implements that functionality.

Processors suitable for the execution of a computer program include, by way of example, both general and special purpose microprocessors. Generally, a processor will receive instructions and data from a read-only memory or a random access memory or both. The essential elements of a computer are a processor for executing instructions and one or more memory devices for storing instructions and data. Information carriers suitable for embodying computer program instructions and data include all forms of non-volatile memory, including by way of example semiconductor memory devices, e.g., EPROM, EEPROM, and flash memory devices; magnetic disks, e.g., internal hard disks or removable disks; magneto-optical disks; and CD-ROM and DVD-ROM disks. One or more memories can store media assets (e.g., audio, video, graphics, interface elements, and/or other media files), configuration files, and/or instructions that, when executed by a processor, form the modules, engines, and other components described herein and perform the functionality associated with the components. The processor and the memory can be supplemented by, or incorporated in special purpose logic circuitry.

In various implementations, a user device includes a web browser, native application, or both, that facilitates execution of the functionality described herein. A web browser allows the device to request a web page or other downloadable program, applet, or document (e.g., from the server(s)) with a web page request. One example of a web page is a data file that includes computer executable or interpretable information, graphics, sound, text, and/or video, that can be displayed, executed, played, processed, streamed, and/or stored and that can contain links, or pointers, to other web pages. In one implementation, a user of the device manually requests a web page from the server. Alternatively, the device automatically makes requests with the web browser. Examples of commercially available web browser software include Google® Chrome®, Microsoft® Internet Explorer®, Mozilla® Firefox®, and Apple® Safari®.

In some implementations, the user devices include client software. The client software provides functionality to the device that provides for the implementation and execution of the features described herein. The client software can be implemented in various forms, for example, it can be in the form of a native application, web page, widget, and/or Java, JavaScript, .Net, Silverlight, Flash, and/or other applet or plug-in that is downloaded to the device and runs in conjunction with the web browser. The client software and the web browser can be part of a single client-server interface; for example, the client software can be implemented as a plug-in to the web browser or to another framework or operating system. Other suitable client software architecture, including but not limited to widget frameworks and applet technology can also be employed with the client software.

A communications network can connect the devices with one or more servers and/or with each other. The communication can take place over media such as standard telephone lines, LAN or WAN links (e.g., T1, T3, 56 kb, X.25), broadband connections (ISDN, Frame Relay, ATM), wireless links (802.11 (Wi-Fi), Bluetooth, GSM, CDMA, etc.), for example. Other communication media are possible. The network can carry TCP/IP protocol communications, and HTTP/HTTPS requests made by a web browser, and the connection between the clients and servers can be communicated over such TCP/IP networks. Other communication protocols are possible.

The system can also be practiced in distributed computing environments where tasks are performed by remote processing devices that are linked through a communications network. In a distributed computing environment, program modules can be located in both local and remote computer storage media including memory storage devices. Other types of system hardware and software than that described herein can also be used, depending on the capacity of the device and the amount of required data processing capability. The system can also be implemented on one or more virtual machines executing virtualized operating systems such as those mentioned above, and that operate on one or more computers having hardware such as that described herein.

In some cases, relational or other structured databases can provide such functionality, for example, as a database management system which stores data for processing. Examples of databases include the MySQL Database Server or ORACLE Database Server offered by ORACLE Corp. of Redwood Shores, Calif., the PostgreSQL Database Server by the PostgreSQL Global Development Group of Berkeley, Calif., or the DB2 Database Server offered by IBM.

It should also be noted that implementations of the systems and methods can be provided as one or more computer-readable programs embodied on or in one or more articles of manufacture. The program instructions can be encoded on an artificially generated propagated signal, e.g., a machine-generated electrical, optical, or electromagnetic signal that is generated to encode information for transmission to suitable receiver apparatus for execution by a data processing apparatus. A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

Sample User Operation

A user may engage the application through a user interface such as a welcome page, directing a user to one or more base products. The interface may have a list or scroll-type option for allowing the user to view one or more products. On a primary page, the user may log in, begin a scan or shop for products. As such a cart feature, log-in feature and scan feature interactive to a user selection would be preferably used. The user would select the next step. IF a scan is initiated, the user will have an interactive guidance (video, sound, vibrations, prompts, etc.) to lead the user through a calibration and scan as noted above. The user may associate the application with a social media website (such as Facebook or Google, etc.) and log-in through such a website or through the application directly to the server. If there is an issue with the log-in, the user may be prompted to try again for a set number of times, be prompted to re-set the password or contact customer service. Once logged in, the user can load an existing profile or asked if the user wishes to order a product. New users are prompted to provide user data for use as OAPTA metadata and which are then encoded in a search key and used to create a user ID.

After selecting a product, or after completing an initial scan (which will include calibration steps), the user will be prompted to select a product (either an existing customized cosmetic formulation from a prior session, or a new product which may be a non-custom product or a new customized cosmetic product (for example if a user has created a foundation, but now wants to create an eye make-up product). Options may be provided for reviewing the user's cart, gift options, reordering, and the like. The application may also prompt a user to run a scan which is preferred for any re-order of more than about thirty (30) days. Once an order is complete, the order is processed. The application may also include an order history, a preview of products being ordered, and product details. As commonly provided by log-in or association of the application with a service such as Facebook, product orders may also be shared through the application with associated social media websites in a typical manner, and friends or other users added as associated as a friend to the user in the application. Other users (known or not known) may be "followed" through the application as well for modifying a user profile and friends may be invited to the application.

In the application, a user preferably may be able to access the user's current beauty profile through a profile tab on a user interface (see FIG. 8) to take the user to the user's beauty profile, wherein the beauty profile is an interface to a search key. The beauty profile allows the user to access user personal data, to re-run a scan which provides updated scan information to be incorporated and encoded into the user's search key, as well as scan settings, and to allow the user also to send gifts, referrals, associate or list friends, seek help support, contact customer service, and provide feedback which may also provide user data collection that the application may associate with OAPTA metadata and update information encoded in a user's search key. Links to running a scan, ordering product and user information profiles may also be placed on the current profile interface.

Modification of the Search Key

The user interface is constructed based on the contents of the search key. The first screen may present, for example, main search components associated with the search key for editing such as color, dryness, opacity, coverage, SPF and/or product finish.

Figure 5:
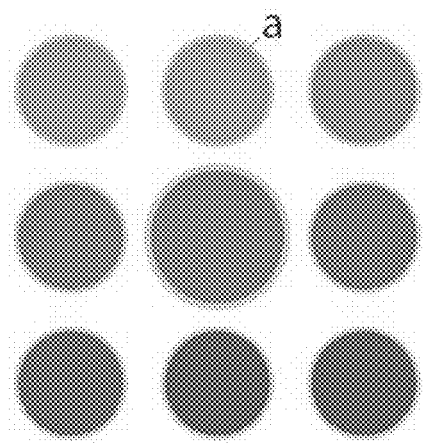
FIG. 5 is a representation of one embodiment of modifying a color component of an initial customized cosmetic product having an initial cosmetic product color, wherein the color variation step is gathered from color neighborhood found by a search key, and the label 'a' shows a first user selection.
Figure 6:
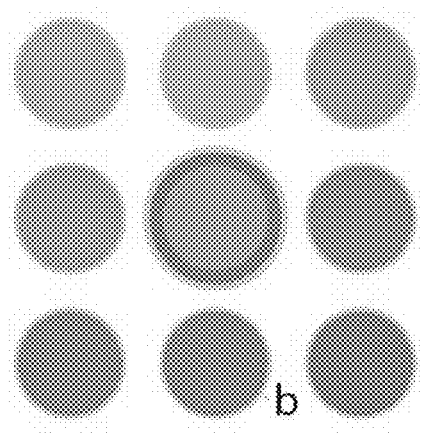
FIG. 6 is a representation of a result of first user selection in FIG. 5, wherein a selected color is moved over the center initial color, and color variation is adjusted, and label 'b' shows second user selection.
Figure 7:
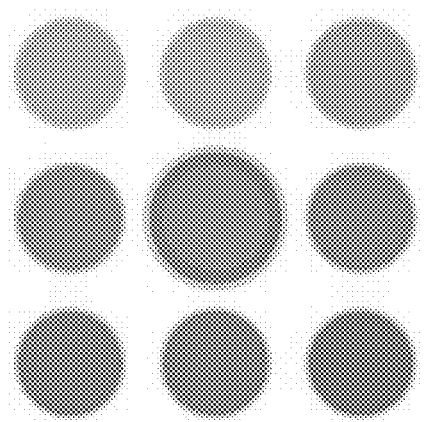
FIG. 7 is a representation of a result of a second user selection, wherein a selected color 'b' of FIG. 6 is moved over the center initial color and color variation is adjusted.

In one embodiment herein, as shown in FIGS. 5-7, if the user selects color for modification, for example, an interface is built so as to show an image of the original color in the center, and variations of color in a pattern around that image of the original color as shown in FIG. 5. The variation of the color pattern may be constructed using data from the OAPTA dataset for the initial customized cosmetic product that was produced for the user, and the statistical record of previous interactions with the color neighborhood being modified. For instance, it may be determined that the most likely change needed is to make the color slightly darker or lighter in luminance, or slightly more orange or less orange. The light/dark colors may be presented vertically, and the less/more orange presented horizontally. Other color choices may surround these choices based on less likely options, such as, more red, or more yellow.

The user may then select the modification that is the closest to his or her need or preference such as selection "a" in FIG. 5. In a further example embodiment, the interface may then show the new color now at the center as in FIG. 6, with the old color next to it. The colors surrounding the new choice "a" of FIG. 6 (now at the center) show slightly smaller and larger color or tone steps based on the last selection, and the most likely choice. If satisfied with "a", the user may then finally select that choice as a final modified customized product and/or may select a further option now shown, such as item "b" of FIG. 6, in which case, that choice "b" would move to the center as in FIG. 7.

Figure 8:
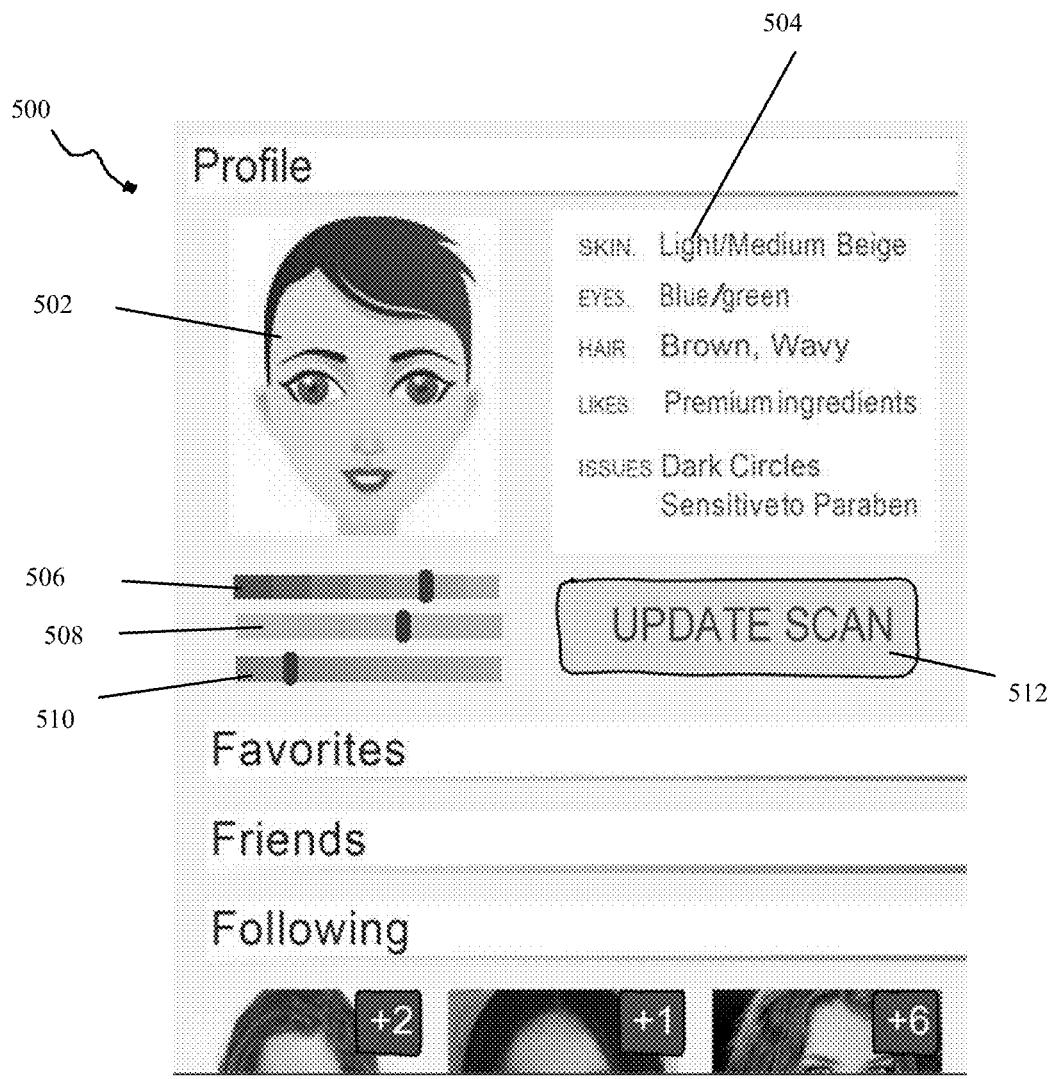
FIG. 8 is an illustration representation of a sample user interface page for use in modifying a user profile for a customized cosmetic product according to a further embodiment herein.

In another embodiment as shown in FIG. 8, a graphical representation of a user interface screen that may be with an application as described herein shows a user profile 500. The profile has a photo (shown as an illustration of a person, but in a real embodiment, a digital photo would preferably appear). The image of the user 502 is optional but useful in showing basic identification of the user and showing the user's characteristics as submitted to the application. The application may also use the photo or a video from the user or the user's scan (or updated scan) and activate associated software for detecting facial feature(s) and/or mapping of a user's face using facial recognition software. The photo is preferably taken from the user survey and/or facial detection software to provide the user with a current display for the user to refer to for evaluating the user's beauty profile and search component features for modification, The interface screen would also preferably include a summary 504 of general characteristics of the user taken from the user data collection and OAPTA metadata information from user feedback, facial detection, facial mapping, scanning survey, user input and from the updated user scans as noted above. In this instance, the user is shown based on the user scans and user input to have a certain skin type ("Light/Medium Beige"), eye color ("Blue/green"), and to have a certain hair type ("Brown/Wavy") (which may be scanned or input by the user photo image data) and user preferences input by the user ("Premium ingredients") and user concern ("Dark Circles" and "Sensitive to Paraben").

The beauty profile 500 as noted above and as shown in FIG. 8 provides an alternative basis for editing the user's search key to modify the user's customized cosmetic product and associated OAPTA specification. The user's image 502 (which as noted above can be updated through an updated scan, facial detection and/or facial recognition software so as to be interactive) and the use of the general profile summary 504 information, includes for use in modification of the search key through at least one or more search components includes one or more sliding scales showing profile characteristics pertaining, for example, as a dark to light slide 506 (for example to measure the amount of melanin and skin tone), a cool to warm color slid 508 (running for example from green/red to blue/yellow tones which choices may be variable), as well as an undertone slide 510 which can relate to the ruddiness or natural tone of the skin which may be used in evaluating sun sensitivity. Other slide or adjustable components may include a dryness component or a coverage component. That is, the user may want to modify the moisturizing capability of a component in the formulation when their skin is drier (such as in the winter). The user may also wish to have a thicker and/or less opaque formulation when wanting additional coverage for a smoother look. Sliders, variation choices, selector buttons and the like may all be used for such modification requests. It is also possible to simply include a feedback page for written or verbal feedback for requested changes from the user. The feedback data can be incorporated into OAPTA metadata derived from user data collection that would then also be utilized as noted above with reference to the initial user customized cosmetic formulation to establish commands encoded on the user's search key to associate with an updated OAPTA specification for preparing a mix and end product based on the modified search key.

The initial user profile can include the summary of the user when the initial profile was completed. The initial profile would represent the user data associated with search components in the search key that is related to the user's data collection in the OAPTA metadata used for creating the OAPTA specification. The profile may relate to an OAPTA that was developed for the user using the application to match the user to the ground truth data set to be closest to an existing commercial product (i.e., a non-customized product) or a customized cosmetic formulation. Whatever the match indicated, it was automatically selected for the user and matched to the user to create the OAPTA specification which is used for the mix and to generate the initial customized cosmetic formulation for the user.

In one embodiment a user may combine product display on the user interface and display of facial feature detection software to provide an interactive interface for the user to engage in interactive editing of search components of a search key (for example, by contacting a region of the image that is detected (such as a cheek area) so that the application can display search components associated with the reference profile of the product displayed on the user's image allowing the user to reference search components of the displayed product for modifying a user's own search components for modifying a user search key and creating a modified or new customized cosmetic product.

Once the user evaluates the customized product, the user may determine, as noted above that the user may wish to try alternatives. For example, the user may wish to get a different coloration profile either for a change in skin tone, aesthetic reasons, or for a different look. The user could then modify search components through the interface to modify the user's search key, such as by using the slides as in FIG. 8 (of the variation color selection circles of FIGS. 5-7) to see how the change in tone might look on an image of the user in the profile screen, in the case where a facial recognition software and make-up try-on application were integrated with the screen, or to use the sliders to initial a new match. In order to do that, the application may ask the user also to "update scan" using the selection 512. The user may also use other application specific data (such as prior favorite products the user may want to order or modify). Users that log-in through social networks, may follow looks that their friends, who may be integrated to the application are using, or friends or other users in the application that the user may be "following" to see what products other users of a similar coloring and look are selecting. Once the user wishes to modify the look or product orders using these various feedback selections, the user would update the scan, and use the sliders (or a color selection screen as described above with respect to FIGS. 5-7) to select a modified profile or a new and separate profile, each of which may be saved to the user's search key and user ID information so as to be available for further orders.

The product may then be re-ordered and manufactured using the modified search key. The primary points of the interaction with the user include that: the user is shown an interface to modify each element of the search key; the variation in selection of each search key component is determined by the neighborhood being modified (whether expressed as a color variation selection screen, sliders or other similar mechanisms); the amount of variance in the neighborhood for that search key component is used to determine the amount of variation presented; the statistical record of requested variation is used to present the direction of the variation presented to the user; additional selections are provided to allow the user to edit less-likely cases; the original, unmodified value is presented next to the current selected value; and the user may optionally update his or her associated search key for future orders.

In another embodiment, a user may wish to modify an existing product that was not produced using custom manufacturing, but that has been characterized by the same system and method as the custom product as noted above.

Thus, while the initial match may have been to a non-custom product for the initial user OAPTA, the user may still wish to modify that formulation. While this characterization may preferably include making the product customizable, it need not do so. The minimal case is that each shade or SKU of the product would be matched with a known user and a known search key. A database of such products is built, searchable by each product SKU, and returning the product's search key.

As mentioned above, a non-customized product may be used to create a search key, that search key may reside in a ground truth database. Thus, the user may also simply decide (even if the user has an existing profile for a customized product) to create a new profile using an existing non-custom product having a SKU (search key) and then modify it. The interaction for this embodiment includes that: the user may use a mobile device, web site or other device to modify the product; the user logs on; the user selects the non-custom product to customize, wherein selection may be by scanning a barcode, from a name search, from a product identification, and/or from a photograph of the product; the search key associated with the non-custom product is found in the ground truth database; and the search key is used to modify and produce new custom product as described in the previous embodiment.

Other options may also be provided for modifying a user profile, including allowing a user to get an initial profile with several options recommended using the reference data and professional group, that may include one or more non-custom commercial products, and one or more customized formulation, each of which was selected by the user data input into the application from the initial user data and scan data. As mentioned above, existing, non-custom product(s) may be associated to a user's search key of a user and also presented to the user via the user interface. The neighborhood of non-custom products associated with search keys in the ground truth database, as disclosed above, may also be associated with the user, and their contribution scalar may be used for display.

In one embodiment of editing a user's search key, these products may displayed as a set of choices. The choices may be ranked by "closest match" value (99% rank, 80% rank, etc.) and displayed either graphically or by using a "try-on" software to allow the user to display the recommendations as ranked on an image of the user. Alternatively, the user may see color shades in graphical display or in an image of a product having a shade key and similar graphical displays to allow the user to choose a desired product. The other choices may be saved to the user search key as alternative choices such that if the initial user selection is determined by the user to not be suitable in a future interaction with the application, the alternative choices may be tried or a new query submitted. Each user interaction preferably includes an updated user scan and user profile review such that the application can detect any changes in the user's skin tone, blemishes, new skin tone change areas, hair color changes, preference changes, etc. The updated scan will also automatically allow the application to interact with the user device to confirm and update for any change in the user's device (new device, updated operating system, updated version of the operating system, etc.), change in software, model number, etc., all of which is saved to the user data. The application will also preferably lead the user through a calibration each time the user re-engages the application to confirm the device data as discussed above and also to confirm the white balance and color data. The application will preferably calibrate using a calibration surface as noted above such as a known user's skin region, a white sheet of paper, etc.

Figure 9:
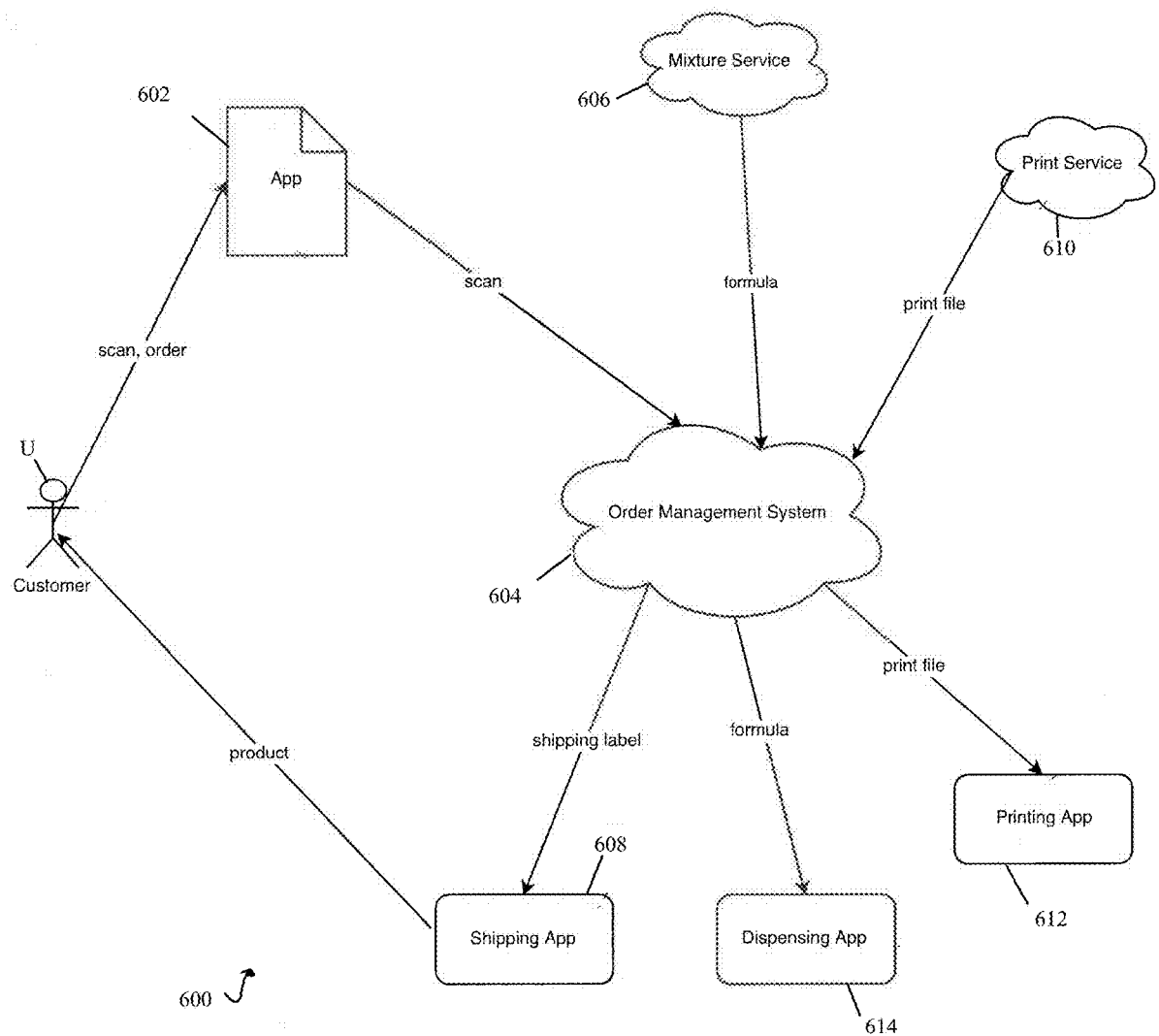
FIG. 9 is a representation of a system for use in creating a customized cosmetic product or modifying a customized cosmetic product.

In a generalized overall system 600 as shown in FIG. 9, a user U interacts with the application 602, wherein the application may be any of the systems and methods described hereinabove, through using a scan and/or ordering a customized cosmetic formulation through the application. The application 602 running on a device having an image sensor and preferably a light source as described above communicates the scan data (including optical data, user information, etc. as described above) to an order management system 604. The order management system and various components thereof, are connected to a server(s) as described above which may reside in specific locations or in a cloud-based or other remote server. The order management system stores the data for the various functions and steps to be carried out as described above. It interacts with a mix service 606 that generates a customized cosmetic formulation, a shipping application 608 which will receive a shipping label incorporating user information from the management system, a printing service 610 that prints data according to the order management system for the user ID and other information on the product as well as on the labels, a printing application 612 that runs the print service and interacts with the management system 604, and a dispensing application 614 that receives instructions from the order management system to dispense and blend the customized cosmetic formulation based on instructions from the mixture service and order management system. A preferred examples of such a system is described in detail in applicant's co-pending application Ser. No. 15/855,064.

This system 600 may also be adapted to carry out the modification of a customized product by sending a rescan from user U using the application 602 and modifying the user search key stored in the user management system 604 and then executing the system based on the modified search key selection. The device re-scan will send the calibrated information as well as the updated user information and instructions for manufacturing. The mix will also be calibrated on each request against model LAB data or other pre-set calibrations for color data. Each pre-mix is tested and calibrated accordingly. Non-custom commercial products included in the data base are also stored based on calibrated LAB data, opacity and shine. Thus the system remains dynamic and responsive to user needs while providing interactive beauty guidance through the match capability based on the user's scan, user input, preferences, and access to the choices that are provided by using the search key to match the user to the ground truth data set having information from both existing non-custom products and reference user data and existing user data incorporating a large number of customized cosmetic formulations to allow for a closest match and creation of a customized cosmetic formulation as well as the ability to modify that customized cosmetic formulation based on a user's request, changes in styles, aesthetics or the user's profile data. The user's profile data (which may be referred to as a beauty profile) can be interactive so as to all the user to transmit questions through the application concerning the profile, so as to drive the most accurate profile and/or to take into account user preferences (cost, brands, components, colors, etc.). Data may be collected from the user interactions through known techniques achieved using website analytics to provide recommendations through the application or to inform the professional service so as to incorporate feedback and further recommendations.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A system for making a modified customized cosmetic product from an initial customized cosmetic product, comprising,
    at least one computer that includes at least one memory for storing computer-executable instructions and at least one processing unit for executing the instructions stored in the at least one memory; and
    a device having an image sensor, a light source and an application installed thereon, wherein execution of the instructions programs the at least one processing unit to perform operation comprising:
    providing a known search key for a user by the application, the application configured to provide the known search key by: capturing at least one image of at least one skin region of the user, processing the at least one image and automatically calibrating settings of the device having the image sensor based on user data and device data from the at least one image, capturing at least one further image of the at least one skin region of the user using the calibrated settings, processing the at least one further image of the skin region of the user to provide calibrated user and device data, and saving the calibrated user and device data in the known search key associated with the user;
    specifying an initial customized cosmetic product having a cosmetic formulation by the known search key, wherein the known search key further comprises at least one search component associated with the initial customized cosmetic product, the at least one search component including one or more of a color component, a coverage component, and a dryness component, and wherein the initial customized cosmetic product associated with the knowns search key is stored in the system as a reference specification having the cosmetic formulation;
    providing a user interface comprising a slider, button, or image for the user to modify at least one of the at least one search components in the known search key;
    receiving an instruction from the user associated with the known search key and the initial customized cosmetic product through the user interface to modify at least one of the at least one search components associated with the cosmetic formulation in the known search key to create a modified search key, wherein the modified search key is also associated with the user and stored in the system, and wherein the user interface provides the user with a selection of a search key component to modify, wherein the selection of the search key component to modify provides a direction for modification that is based on a past likelihood of direction for modification;
    processing the modified search key to automatically determine a modified customized cosmetic product for the user by evaluating a neighborhood of closest keys and storing the modified customized cosmetic product associated with the modified search key in the system in a reference specification having a modified cosmetic formulation; and
    processing the modified search key to determine manufacturing instructions for making the modified customized cosmetic product.

2. The system according to claim 1, wherein the at least one search component comprises a color component.

3. The system according to claim 1, wherein the at least one search component comprises a coverage component.

4. The system according to claim 1, wherein the at least one search component comprises a dryness component.

5. The system according to claim 1, wherein the at least one search component includes each of a color component, a coverage component, and a dryness component.

6. The system according to claim 1, wherein a user interaction amount provided by the user interface is based on a change of a search key component within the neighborhood of closest keys in the system.

7. The system according to claim 1, wherein the manufacturing instructions comprise amounts of cosmetic primary components, and wherein each cosmetic primary component is a valid cosmetic product that meets applicable regulatory requirements.

8. The system according to claim 7, wherein one of the at least one search components is a SPF.

9. The system according to claim 7, wherein two cosmetic primary components are made and recorded to verify proportions of the cosmetic primary components in a record.

10. The system according to claim 9, wherein customer contact information is associated with the record.

11. The system according to claim 1, wherein the user interface is associated with the device having the image sensor and the application can be initiated before the user interaction to calibrate the device settings and to capture at least one updated user image using the calibrated device settings to submit updated user and device data to the system for updating data associated with the known search key, and wherein the updated user and device data is employed in the system to optimize the known search key for use in modifying the known search key to create the modified search key.

12. The system according to claim 1, wherein the system comprises a ground truth database and the initial customized cosmetic product of the known search key in the reference specification is also associated to a non-custom product, and wherein the known search key, the initial customized cosmetic product, and the non-custom product are each stored in the ground truth data base.

13. The system according to claim 1, wherein the system comprises a ground truth database and the initial customized cosmetic product of the known search key in the reference specification is a customized cosmetic product, and the initial customized cosmetic product and the known search key are stored in the ground truth data base.

14. The system according to claim 1, wherein the system comprises a ground truth database and the modified customized cosmetic product having the modified search key is also associated with a non-custom product in the modified reference specification stored in the ground truth data base and wherein the operations further comprise associating the modified customized cosmetic product and the non-custom product with the user.

15. The system according to claim 1, wherein the system comprises a ground truth database and the modified customized cosmetic product having the modified search key is a customized cosmetic product in the modified reference specification stored in the ground truth data base and the operations further comprise associating the modified customized cosmetic product with the user.

16. The system according to claim 1, wherein the application calibrates the device having the image sensor based on the device data to control at least one device setting selected from the group consisting of aperture, exposure, exposure time, focus, sensitivity, and/or white balance.

17. The system according to claim 1, wherein the system comprises a ground truth database, the initial customized cosmetic product and the modified custom cosmetic product are included in a ground truth database, and the system further comprises an order management service, a mixture service, a print service, a dispensing application, a shipping application, and a printing application.

18. A method for modifying a customized cosmetic product associated with a user, comprising:
providing a system comprising at least one computer that includes at least one memory for storing computer executable instructions and at least one processing unit for executing the instruction stored in the at least one memory and a device having an image sensor, a light source and an application installed thereon, wherein execution of the instructions programs the at least one processing unit to perform operations in the method:
providing a known search key for a user by the application on the device having the image sensor, wherein providing the known search key comprises to capturing at least one image of at least one skin region of the user, processing the at least one image and automatically calibrating settings of the device having the image sensor based on user data and device data from the at least one image, capturing at least one further image of the at least one skin region of the user using the calibrated settings, processing the at least one further image of the skin region of the user to provide calibrated user and device data, and saving the calibrated user and device data in the known search key associated with the user;
specifying an initial customized cosmetic product having a cosmetic formulation by the known search key, wherein the known search key further comprises at least one search component associated with the initial customized cosmetic product, the at least one search component including one or more of a color component, a coverage component, and a dryness component, and wherein the initial customized cosmetic product associated with the knowns search key is stored in the system as a reference specification having the cosmetic formulation;
providing a user interface comprising a slider, button, or image for the user to modify at least one of the at least one search components in the known search key;
receiving instructions from the user associated with the known search key and the initial customized cosmetic product through the user interface to modify at least one of the at least one search components associated with the cosmetic formulation in the known search key to create a modified search key, wherein the modified search key is also associated with the user and stored in the system, and wherein the user interface provides the user with a selection of a search key component to modify, wherein the selection of the search key component to modify provides a direction for modification that is based on a past likelihood of direction for modification;
processing the modified search key to automatically determine a modified customized cosmetic product for the user by evaluating a neighborhood of closest keys and storing the modified customized cosmetic product associated with the modified search key in the system in a reference specification having a modified cosmetic formulation; and
processing the modified search key to determine manufacturing instructions for making the modified customized cosmetic product.

19. The method for modifying a customized cosmetic product according to claim 18, wherein the initial customized cosmetic product having the known search key that is stored in the reference specification having the cosmetic formulation is stored in a ground truth database and is also associated with a non-custom product.

20. The method for modifying a customized cosmetic product according to claim 18, wherein the modified customized cosmetic product having the modified search key that is stored in the reference specification having the modified cosmetic formulation is stored in a ground truth data base and also associated with a non-custom product, and the method further comprises associating the modified customized cosmetic product and the non-custom product with the user.

21. The method for modifying a customized cosmetic product according to claim 18, wherein the modified customized cosmetic product having the modified search key that is stored in the reference specification having the modified cosmetic formulation is a customized cosmetic product and is stored in the ground truth database.

22. The method for modifying a customized cosmetic product according to claim 18, wherein the at least one search component comprises a color component, a coverage component, and a dryness component.

23. The method for modifying a customized cosmetic product according to claim 18, wherein the user interface includes one or more sliders for the selection of the search key component to modify, and each slider is associated with a search component.

24. The method for modifying a customized cosmetic product according to claim 18, wherein the user interface includes one or more close alternative choice icons displayed adjacent to an icon representing one of the at least one search components of the known search key for the selection of the search key component to modify and the method further comprises a user selecting one of the close alternative choice icons for modifying the search component.

25. The method for modifying a customized cosmetic product according to claim 18, wherein the device having the image sensor comprises the user interface.

26. The method for modifying a customized cosmetic product according to claim 25, further comprising initiating the application before the user interaction to calibrate the device settings and to capture at least one updated user image using the calibrated device settings to submit updated user and device data to the system for updating data associated with the known search key, and wherein calibrating the device settings includes controlling at least one device setting selected from the group consisting of aperture, exposure, exposure time, focus, sensitivity, and/or white balance.

* * * * *